United States Patent
Omura

(10) Patent No.: US 9,326,747 B2
(45) Date of Patent: May 3, 2016

(54) MOBILE RADIATION IMAGING APPARATUS AND MOBILE RADIATION IMAGING SYSTEM

(71) Applicant: CANON KABUSHIKI KAISHA, Tokyo (JP)

(72) Inventor: Satoru Omura, Chigasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 90 days.

(21) Appl. No.: 14/038,385

(22) Filed: Sep. 26, 2013

(65) Prior Publication Data

US 2014/0093040 A1  Apr. 3, 2014

(30) Foreign Application Priority Data

Sep. 28, 2012  (JP) ................. 2012-215966

(51) Int. Cl.
*A61B 6/00* (2006.01)
*H05G 1/02* (2006.01)

(52) U.S. Cl.
CPC ............... *A61B 6/547* (2013.01); *A61B 6/4405* (2013.01); *A61B 6/4452* (2013.01); *A61B 6/54* (2013.01)

(58) Field of Classification Search
CPC ......... A61B 6/4405; A61B 6/54; A61B 6/547
See application file for complete search history.

(56) References Cited

U.S. PATENT DOCUMENTS

| | | | | |
|---|---|---|---|---|
| 4,326,131 A * | 4/1982 | Waerve | ................. | H05G 1/02 378/193 |
| 7,023,959 B2 * | 4/2006 | Nakagawa | ........... | A61B 6/4405 378/98 |
| 7,581,884 B1 | 9/2009 | Barnes et al. | | |
| 2003/0190014 A1 * | 10/2003 | Nakagawa | ........... | A61B 6/4405 378/193 |
| 2003/0198317 A1 * | 10/2003 | Nakagawa | ........... | A61B 6/4405 378/62 |
| 2004/0042587 A1 * | 3/2004 | Deshpande | ............ | A61B 6/105 378/198 |
| 2006/0120512 A1 * | 6/2006 | Watanabe | ............ | A61B 6/4405 378/198 |
| 2008/0013692 A1 | 1/2008 | Maschke | | |
| 2010/0296632 A1 * | 11/2010 | Bouvier | ............... | A61B 6/4405 378/198 |
| 2010/0329426 A1 * | 12/2010 | Oda | ...................... | A61B 6/4283 378/98.2 |
| 2011/0249807 A1 * | 10/2011 | Dirisio | ................ | A61B 6/4405 378/198 |
| 2012/0093298 A1 * | 4/2012 | Lalena | .......................... | 378/198 |
| 2013/0064351 A1 * | 3/2013 | Urbon | .................. | A61B 6/4405 378/98.5 |

FOREIGN PATENT DOCUMENTS

| | | |
|---|---|---|
| CN | 1433333 A | 7/2003 |
| CN | 1550212 A | 12/2004 |
| EP | 1479343 A1 | 11/2004 |
| JP | 2003012292 A | 1/2003 |
| JP | 2006-055434 A | 3/2006 |
| JP | 200681690 A | 3/2006 |
| JP | 2007313252 A | 12/2007 |
| JP | 2008259881 A | 10/2008 |
| JP | 2009022677 A | 2/2009 |
| JP | 2009039332 A | 2/2009 |
| JP | 2012-005731 A | 1/2012 |
| WO | WO 2011136094 A1 * | 11/2011 ........... A61B 6/4405 |

* cited by examiner

*Primary Examiner* — Michael Logie
(74) *Attorney, Agent, or Firm* — Canon USA Inc. IP Division

(57) ABSTRACT

A mobile radiation imaging apparatus includes a radiation generation unit configured to generate radiation, a cart, a supporting member formed on the cart and configured to hold the radiation generation unit in a movable manner with respect to the cart, a detection unit configured to detect arrangement of the radiation generation unit in a particular non-imaging position, and a control unit configured to limit a motion of the supporting member according to a detection result by the detection unit.

28 Claims, 14 Drawing Sheets

MOBILE RADIATION IMAGING APPARATUS AND MOBILE RADIATION IMAGING SYSTEM

BACKGROUND

Technical Field

The present invention relates to a radiation imaging apparatus used for obtaining a radiation image of a subject by exposing the subject to radiation and detecting a resulting radiation image.

In recent years, mobile X-ray imaging apparatuses useful in capturing X-ray images in a hospital room or an operating room as well as apparatuses with an X-ray tube for projecting X-rays from a C-beam and an X-ray detector for detecting an X-ray image as a result of the projection are widely used as X-ray imaging apparatuses for medical care.

When an X-ray image of a subject is taken by a mobile X-ray imaging apparatus, an X-ray tube is placed at a position above a subject lying on a bed. X-ray images appropriate for diagnosis are obtained when good positioning of the X-ray detector and the X-ray tube for the imaging portion of the subject is achieved.

Although the mobile X-ray imaging apparatus passes through a small space between beds in hospital rooms and corridors of hospital wards where stretchers and other medical apparatuses come and go, the beam of the mobile X-ray imaging apparatus that holds the X-ray tube is widely extended when the X-ray imaging is performed. According to the X-ray imaging apparatus discussed in Japanese Patent Application Laid-Open No. 2006-81690, the beam that holds the X-ray tube is extendable. However, if a mobile radiation imaging apparatus has a beam which can be freely extended, the beam may collide with other members of the apparatus or collide with other structures around the apparatus. This may cause damage or malfunction.

SUMMARY

According to an aspect of the present invention, a mobile radiation imaging apparatus includes a radiation generation unit configured to generate radiation, a cart, a supporting member formed on the cart and configured to hold the radiation generation unit in a movable manner with respect to the cart, a detection unit configured to detect arrangement of the radiation generation unit in a particular non-imaging position, and a control unit configured to limit a motion of the supporting member according to a detection result by the detection unit. The control unit stops the supporting member (such as a beam) from extending when not in use and thus reduces the risk of collision of the supporting member with other pieces of apparatus.

Further features of the present invention will become apparent from the following description of exemplary embodiments with reference to the attached drawings.

DESCRIPTION OF THE EMBODIMENTS

Figure 1:
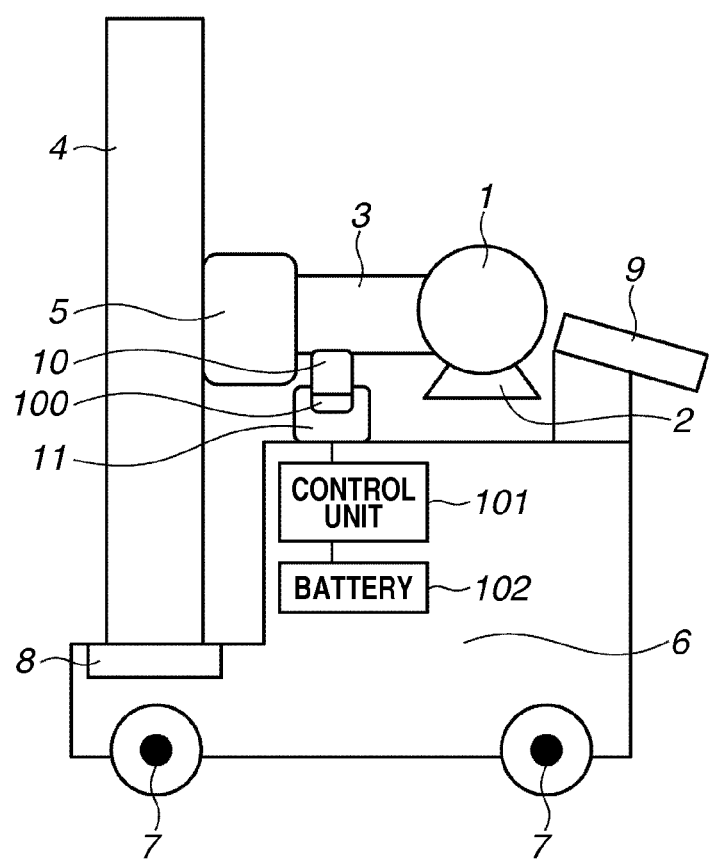
FIG. 1 illustrates a configuration of a mobile X-ray imaging apparatus according to an exemplary embodiment of the present invention.

FIG. 1 illustrates a configuration of a mobile X-ray imaging apparatus according to an exemplary embodiment.

In FIG. 1, an X-ray tube 1 is a radiation generation unit which generates and emits X-rays. The X-ray tube 1 is fixed to a setting member or a supporting member. Since the X-ray tube 1 is used for performing various types of imaging, the position and the orientation of the X-ray tube needs to be changed according to the imaging style. The setting member is used for changing the position of the X-ray tube and setting the irradiated range of radiation. The supporting member is set on a cart (or trolley) portion 6, which is a cart. The supporting member holds the X-ray tube 1 in such a manner that the X-ray tube can be moved relative to the cart portion 6. The setting member or the supporting member includes, for example, a collimator 2, a beam 3 which holds the X-ray tube 1, and a support column 4 which indirectly holds the X-ray tube 1. Additionally, the setting member can be a member used for changing the position and orientation of the radiation generation unit and setting the irradiated range of radiation.

When the X-ray imaging apparatus is in a non-imaging state, for example, in the standby state or when the operator is moving the apparatus to another location, it is important to reduce the size of the whole X-ray imaging apparatus. This is because if the X-ray imaging apparatus collides with a structure in the hospital, the mobile X-ray imaging apparatus itself or the other structure may be adversely affected by the collision. Thus, when the operator moves the X-ray imaging apparatus to another location, for example, the operator retracts the beam 3 so that the beam 3 is lowered with respect to the support column 4 and the X-ray tube 1, which is arranged at a particular non-imaging position (i.e. a home position or a storage position). A detection sensor 100 is a contact sensor which detects whether the X-ray tube 1 is in the non-imaging position by detecting contact of the beam 3 with the cart portion 6. The detection sensor 100 is placed, for example, on the beam 3 or on the cart portion 6 at a position facing the beam 3. When the detection sensor 100 detects the contact, a detection signal is generated as a result of the detection, and the detection signal is output to a control unit 101. The detection signal may be generated only when the beam 3 contacts the cart portion 6. Further, the detection signal may be generated when the beam 3 contacts the cart portion 6, or the signal indicating "contact not detected" may be generated when the beam 3 does not contact the cart portion 6. Furthermore, the detection signal may not be generated if the contact is instantaneous. In other words, the detection signal may be generated only when the contact is continuously detected for a predetermined period of time or by a predetermined pressure.

On receiving the detection signal, the control unit 101 limits at least one motion of the setting member. For example, the control unit 101 inhibits the extension motion of the beam 3 or inhibits the elevating motion of the beam 3 along the support column 4. If the control unit 101 limits one motion of the setting member, according to the example illustrated in FIG. 1, for example, even if the beam 3 is extended from the home position, collision of the X-ray tube 1 (radiation generation unit) with a monitor 9 can be avoided. Further, since the elevation of the beam 3 is inhibited, collision of the beam 3 with the cart portion 6 can also be avoided.

Next, the setting member will be described. The collimator 2 limits the irradiated range of X-rays of the X-ray tube 1. The beam 3 is a supporting member which is cylindrical or pole-shaped and extends in the horizontal direction. The beam 3 holds the X-ray tube 1 at its one end. According to an exemplary embodiment, the beam 3 includes at least an extension mechanism which moves the X-ray tube 1 in the horizontal direction and an extended position fixing mechanism. The support column 4 is a supporting member which is cylindrical or pole-shaped and extends in the vertical direction. The support column 4 holds the beam 3. A beam supporting unit 5 connects one end of the beam 3 (the end other than the one fixed to the X-ray tube 1) with a side face of the support column 4. The beam supporting unit 5 includes a unit which allows movement of the beam 3 along the support column 4 and a unit which allows fixing of the beam 3 to an arbitrary position after the movement. The cart portion 6 holds the support column 4. A mobile mechanism 7 allows movement of the cart portion 6 and includes a plurality of tires or casters. The mobile mechanism 7 moves the cart portion 6 by rotating the tires or casters while they contact the ground. A support column rotation unit 8 connects the cart portion 6 and the support column 4. With a bearing mounted in the support column rotation unit 8, the support column 4 can rotate on the cart portion 6 around an axis perpendicular to the ground.

Since an off brake is provided on the support column rotation unit 8 and other setting members, the rotation of the support column 4 can be stopped at an arbitrary position according to the energizing state of the off brake. The off brake is energized by the control unit 101 and enables the limited motion only when it receives a particular signal from the control unit 101. The off brake is an example of a motion limiting member which is called a deadman lock motion limiting member. If the motion limiting member employing the deadman lock is used, when power is supplied to the mobile X-ray imaging apparatus by a power feeding unit such as a battery 102, the control unit 101 enables the limited motion by not supplying power to the motion limiting member of the setting member in a selective manner. According to the motion-limiting member, possibility of runaway of the apparatus can be reduced and a highly safe mobile radiation imaging apparatus can be realized.

If the beam 3, which holds the X-ray tube 1, is extendable and at the home position, the control unit 101 can limit the extension of the beam 3. If the control unit 101 limits the extension of the beam 3, the possibility of the X-ray tube 1 colliding with a monitor 9 can be reduced.

If the above-described beam 3 is supported by the support column 4 in an elevatable manner, the control unit 101 limits the downward motion of the X-ray tube 1 if the beam 3 is at the home position. As for the upward motion, since it is considered as a safe motion of the X-ray tube 1 from the storage position, it is permitted by the control unit 101. If only the downward motion is to be limited, a load sensor that detects an operational force of the operator with respect to the beam 3 may be provided on the beam supporting unit 5. Then, for example, if a load equal to or greater than a particular threshold value is applied upward, the control unit 101 transmits power to the motion limiting member employing the deadman lock and allows the movement. On the other hand, if a load is applied downward, the control unit 101 does not energize the motion-limiting member and limits the downward movement.

If the above-described support column 4 is extendable and employs a multi-stage configuration, the control unit 101 can limit the extension of the support column 4 if the X-ray tube 1 is at the home position. The control unit 101 can limit both the extension and contraction movement of the support column. The movement from the storage position to the non-storage position can be performed by the elevation of the beam 3. This is because, if the height of the support column 4 is too high, it may hit the ceiling. Thus it is important to maintain compact size in the height direction. As is with the above-described beam 3, the control unit 101 may allow only the extension of the support column 4 and limit the retraction of the support column 4. This is effective for a mobile radiation generating apparatus having the support column 4 without the elevation function of the beam 3. If the beam 3 and the support column 4 are elevated at the same time, the setting of the apparatus can be performed faster and the X-ray tube 1 can be efficiently operated.

Further, if the above-described support column 4 is rotatable in the axial direction, the control unit 101 can limit the rotation of the support column 4 when the X-ray tube 1 is at the home position. Accordingly, the possibility of a guiding rod 10 and a guiding rod-receiving unit 11 being damaged by unexpected contact due to the rotation of the support column 4 can be reduced.

Further, a motion limiting member different from the above-described deadman lock motion limiting member can be used. As is an electromagnetic brake, such a motion-limiting member limits the operation of the setting member if it receives power or a particular signal from the control unit 101. For example, if the apparatus is configured such that the positioning of the setting member is manually performed, the setting member will be fixed according to friction between the setting members. With respect to an operational force applied by the operator, the motion of the setting member will be limited according to an electromagnetic brake controlled by the control unit 101.

The monitor 9 is a display unit which displays information. The monitor 9 is provided on the upper face side of the cart portion 6. By the control of the control unit 101, the monitor 9 displays information of the patient being the subject, a place where the patient is, and an inspection information list. The information displayed on the monitor 9 includes subject information obtained from an external radiology information system (RIS) via a communication unit (not illustrated) and image information to be sent to external picture archiving & communication systems (PACS) by the communication unit. Further, the setting of the imaging conditions and the imaging-completed X-ray images can be transmitted to a network in the hospital via the monitor 9. A position-detecting device such as a touch panel can be provided on the monitor 9. The position-detecting device detects a contact position and outputs a signal used for using the display information. Thus, the operator can use the information displayed on the monitor 9.

The guiding rod 10 protrudes from the beam 3 or the X-ray tube 1. The guiding rod-receiving unit 11 is provided on the cart portion 6. The guiding rod 10 fits in the guiding rod-receiving unit 11. The guiding rod 10 guides the beam 3 and the X-ray tube 1 to the storage position when the operator moves the apparatus to another location. A contact sensor 100 is provided on the guiding rod 10 or the guiding rod-receiving unit 11. The contact sensor 100 detects whether the guiding rod 10 is fitted in the guiding rod-receiving unit 11.

Figure 2:
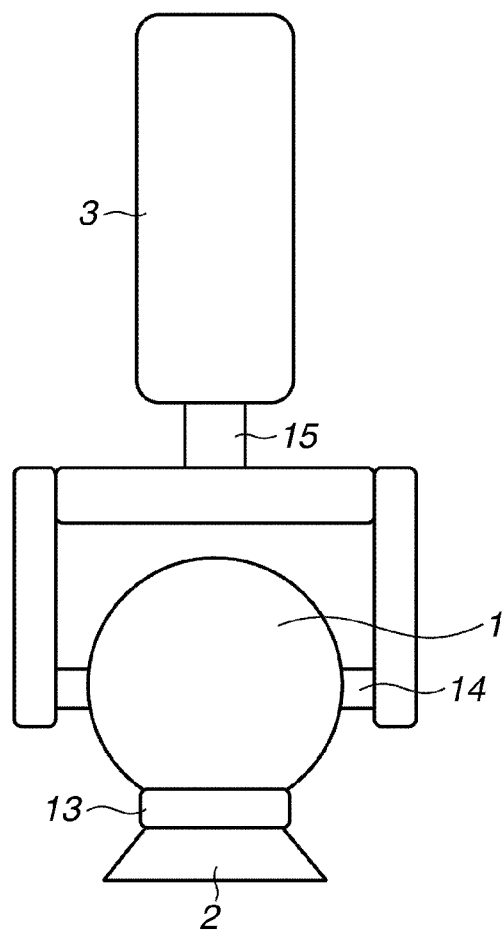
FIG. 2 illustrates a configuration of an X-ray generation unit and surrounding components.

FIG. 2 illustrates a detailed configuration of the X-ray tube 1. A collimator rotation mechanism 13 is a mechanism by which the collimator 2 rotates with respect to the X-ray tube 1. The collimator rotation mechanism 13 can rotate the X-ray emission area while maintaining the shape of the irradiation field limited by the collimator 2. An X-ray tube tilting mechanism 14 tilts the X-ray tube 1. A generation unit-rotation mechanism 15 is a mechanism by which the X-ray tube 1 rotates around an axis in the length direction of the beam 3. Each of the rotation mechanisms 13 to 15 includes a rotation-stopping unit and includes an off brake. An electro permanent magnetic holder can be used for the rotation-stopping unit. If an electro permanent magnetic holder is used, the rotating shaft of each of the rotation mechanisms 13 to 15 may be attracted to the magnet in order to be held in position. The electro permanent magnetic holder is an example of the motion-limiting member which limits a motion when it is energized.

The contact sensor 100 on the guiding rod 10 or the guiding rod accepting unit 11 detects whether the X-ray tube 1 is at the predetermined storage position, which is the position of the X-ray tube 1 when the apparatus is moved to another location. If the contact sensor 100 detects that the X-ray tube 1 is at the storage position, the control unit 101 can stop the rotation of the rotation mechanisms 13 to 15.

The collimator 2, which is one of the setting members, can rotate with respect to the emission direction by use of the rotation mechanism 13. The collimator 2 can shape a bundle of radiation beams into a circular or a square field. If a bundle of radiation beams is shaped into a square field in the emission direction by the collimator 2, even if a radiation detector, which detects a rectangular detection area, is arranged at a position and orientation according to the imaging style, an appropriate emission area can be set. The control unit 101 can limit the rotation of the collimator 2 with respect to the direction of emission. Since the rotation of the collimator 2 is limited, the possibility of the collimator 2 colliding with, for example, the monitor 9 or a fixing member of the monitor 9 can be reduced. If there is no possibility of the collimator 2 colliding with the monitor 9 or a different member of the mobile radiation imaging apparatus according to the rotation of the collimator 2, the control unit 101 does not limit the rotation of the collimator 2.

The X-ray tube tilting mechanism 14, which is one of the setting members, can tilt the X-ray tube 1. Tilting is a rotating motion of the X-ray tube 1 around an axis which passes near the center of the X-ray tube 1 and is orthogonal to the emission direction. The control unit 101 can limit the tilt motion of the X-ray tube 1 by the X-ray tube tilting mechanism 14. By limiting the tilt motion, for example, the possibility of the X-ray tube 1 colliding with a member such as the monitor 9 can be reduced.

The generation unit rotation mechanism 15, which is one of the setting members, allows the X-ray tube 1 to rotate with respect to the axial direction of the beam 3. The control unit 101 can limit the rotation of the X-ray tube 1 performed by the generation unit rotation mechanism 15. Since the rotation of the X-ray tube 1 is limited, the possibility of the X-ray tube 1 or the beam 3 colliding with other members of the mobile radiation imaging apparatus can be reduced. The guiding rod 10 and the guiding rod-receiving unit 11 contact each other when they are in the storage position. If a heavy load is applied to the guiding rod 10 and the guiding rod-receiving unit 11, they may also be damaged.

In addition to the above-described positions, the storage position or the non-imaging position may be any one of a position predetermined as the position of the radiation generation unit when the mobile radiation imaging apparatus is spacially displaced, a position of the radiation generation unit when the mobile radiation imaging apparatus is in the irradiated range, and a position of the radiation generation unit when the radiation by the radiation generation unit is limited. In each case, if the X-ray tube 1 is at the storage position, motion of the setting members other than safely moving the X-ray tube 1 to a non-storage position will be inhibited by the control unit 101. Thus, impact on the mobile X-ray imaging apparatus is reduced and usability will be improved. Further, if the X-ray tube 1 is in the storage position, a drawing or an icon which is useful for the operator in safely moving the X-ray tube 1 from the storage position may be displayed on the monitor 9 according to the control of the control unit 101.

Figure 3:
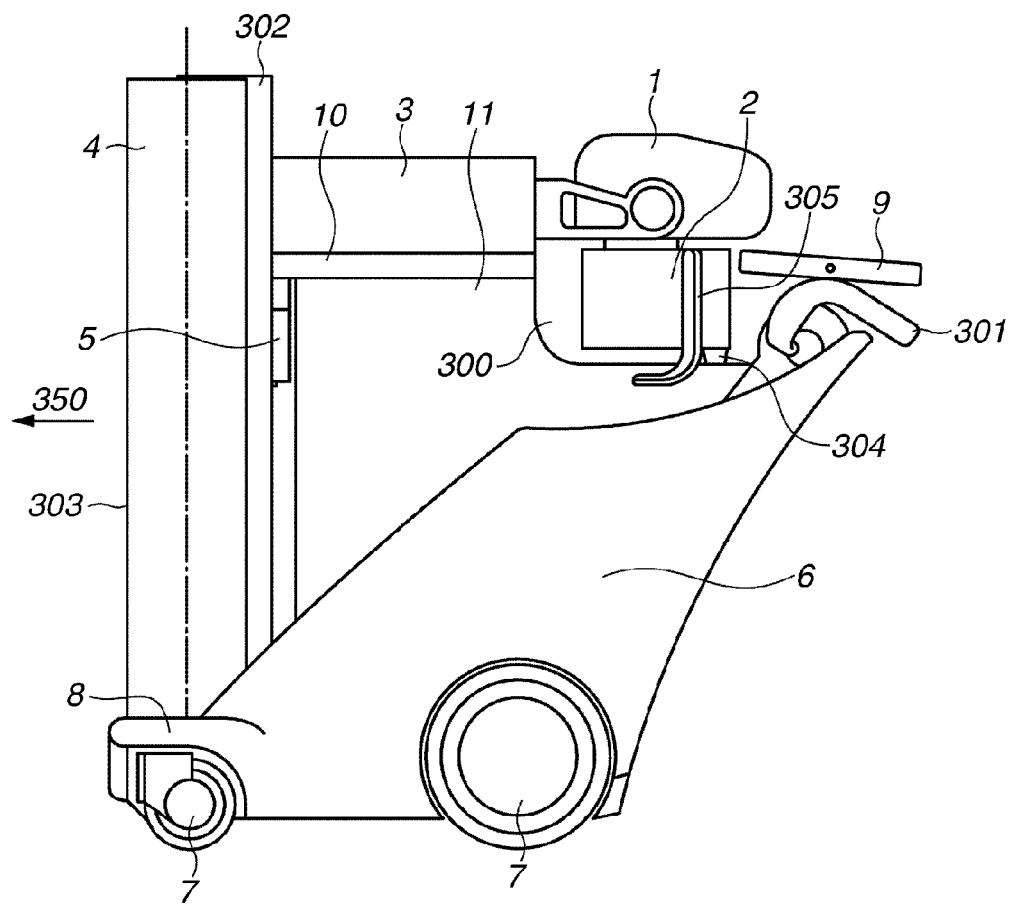
FIG. 3 is an external view of the mobile X-ray imaging apparatus according to an exemplary embodiment.
Figure 4:
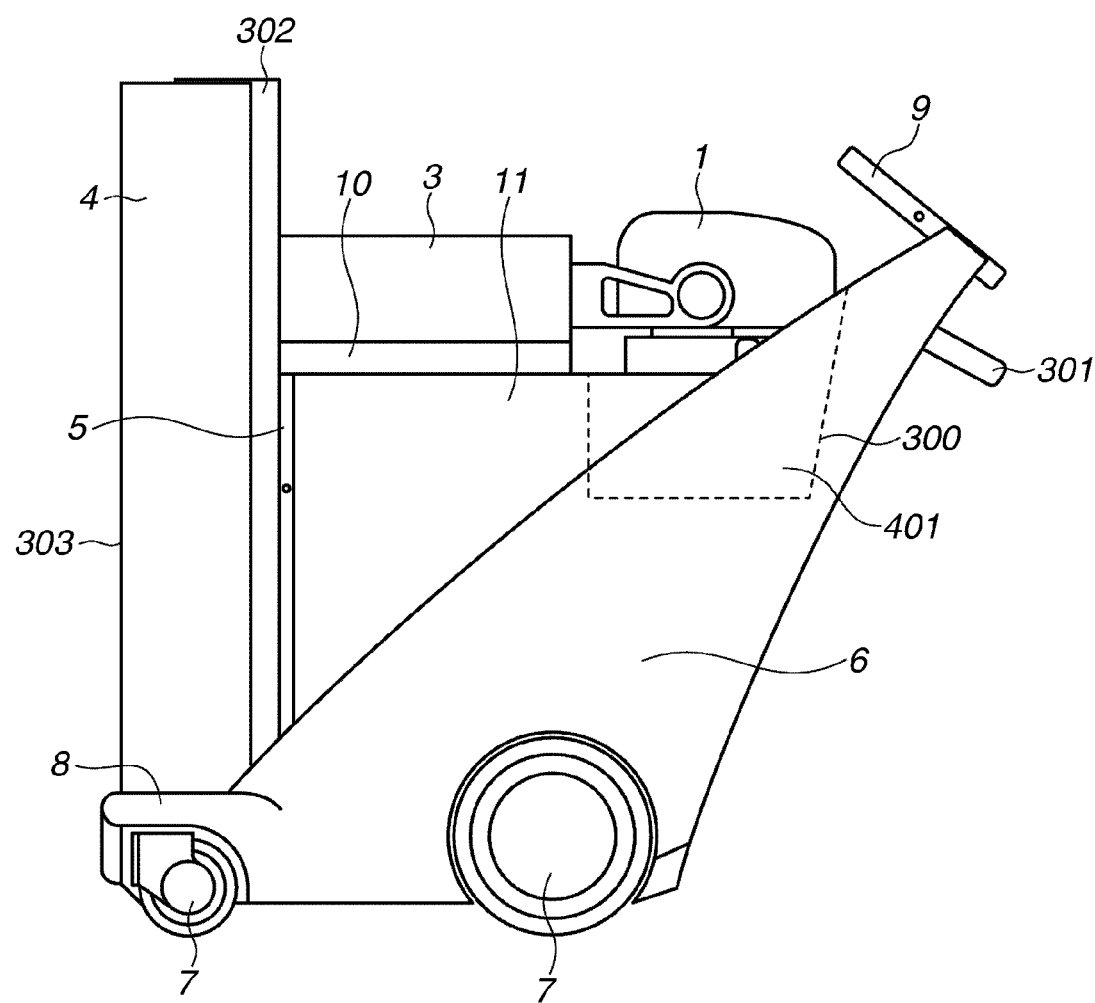
FIG. 4 is an external view of the mobile X-ray imaging apparatus according to another exemplary embodiment.

FIGS. 3 and 4 are external views of the mobile radiation imaging apparatus according to an exemplary embodiment. The components denoted by the same reference numerals as those in FIGS. 1 and 2 indicate that they are similar components.

A handle 301 is a member which the operator of the mobile radiation imaging apparatus holds when the operator moves the cart portion 6. Although not illustrated in detail in FIG. 3, the handle 301, which is provided along the periphery of the monitor 9, is U-shaped when viewed from above. According to the example illustrated in FIG. 3, when the operator moves the mobile radiation imaging apparatus by the handle 301, the operator faces forward in a forward moving direction 350.

The collimator 2 is fixed to an opening of the X-ray tube 1 through which radiation is emitted. The X-ray tube 1 is an example of a radiation generation unit. Shaped radiation beams are emitted from the emission face at the bottom of the collimator 2. A recessed portion 300 is formed with its vertical height reduced in part of the mobile radiation imaging apparatus with respect to the forward moving direction 350. The collimator 2 can be stored in the recessed portion 300. This position of the collimator 2 in the recessed portion 300 can be called as a non-imaging position (storage position, home position).

When the collimator 2 is set in the recessed portion 300 at the home position, the X-ray tube 1 and the collimator 2 are arranged at lower positions. Thus, the possibility of the forward view being blocked by the X-ray tube 1, the collimator 2, and the beam 3 is reduced and the operator is offered a better view. The recessed portion 300 is a portion recessed with respect to the upper face of the cart portion 6 which the beam unit 3 contacts and the upper face of a monitor fixing unit to which the monitor 9 is fixed. On the other hand, the recessed portion 300 may not be concave-shaped in the direction that crosses the forward moving direction 350. According to such configuration, when the X-ray tube 1 is moved from the home position, the contact of the X-ray tube 1 and the collimator 2 with the cart portion 6 can be avoided even if the X-ray tube 1 and the collimator 2 are moved by the rotation of the support column 4 according to the support column rotation unit 8. Accordingly, the control unit 101 does not necessarily limit the rotation motion of the support column 4 and allows the rotation even when the X-ray tube 1 is in the non-imaging position. In this manner, the convenience of the mobile radiation imaging apparatus is improved.

The bottom face of the recessed portion 300 may be protected by a shield member which absorbs or reflects the radiation may so that the X-ray that leaks from the X-ray tube 1 does not adversely affect the control unit 101 and the battery 102 inside the cart portion 6. Further, the shield member may be attached to the inner side of the bottom face, that is, inside the cart portion 6 and on the back side of the bottom face of the member which forms the recessed portion 300.

As illustrated in FIG. 3, a protruding portion 304 which protrudes toward the emission direction is provided on the emission face side of the collimator 2. When the X-ray tube 1 is in the non-imaging position, the protruding portion 304 contacts, for example, the upper face of the recessed portion 300 formed in the cart portion 6 of the mobile radiation imaging apparatus. The protruding portion 304 functions as a stopper and contributes to reducing the possibility of the emission face of the collimator 2 being damaged by the upper face of the cart portion 6. By using an elastic member such as rubber or a buffer member for the protruding portion 304, the impact on the collimator 2 or the upper face of the cart portion 6 can be reduced. A plurality of protruding portions can be used as the protruding portion 304 and placed in an area outside the irradiated range. Further, a stopper member having a protruding portion or having a similar function can also be provided on the X-ray tube 1 and the beam 3.

Further, as illustrated in FIG. 3, a pair of collimator handles 305 can be fixed to the side faces of the collimator 2. By gripping the pair of collimator handles 305, the operator can easily rotate the collimator 2 or move the various setting members used for the positioning of the X-ray tube 1. Further, the pair of collimator handles 305 can extend in the direction of emission further away from the emission face of the collimator 2 than the protruding portion 304. In this case, the pair of collimator handles 305 may have the functionality of the above-described protruding portion 304. Further, it may be configured such that the height of the upper face of the cart portion 6 is reduced along the pair of collimator handles 305.

As illustrated in FIG. 3, if the recessed portion 300 is not concave-shaped in the direction perpendicular to the forward moving direction 350, the pair of collimator handles 305 is exposed at the non-imaging position (storage position) so that the operator can grip the handles. Accordingly, the operator can easily operate the X-ray tube 1 by manipulating the pair of collimator handles 305.

The beam 3 employs a pantograph or a telescopic structure and is thus extendable. According to the example illustrated in FIG. 3, the beam 3 is a four-part extension beam with three extendable beams employing the nested or telescopic structure. The beam 3 includes a first part elevatably fixed to the support column 4, a second part movably engaged in the first beam unit, a third part movably engaged in the second part, and a fourth part movably engaged in the third part. The X-ray tube 1 is fixed to one end of the fourth part. Further, the beam 3 can be formed by four or more movable parts, for example, five or six parts. If the maximum length of the beam 3 is fixed, the more the number of parts is increased, the more the length of the part is decreased. If a beam is made of four parts including three extendable parts, the maximum length of the beam will be the distance from the support column to the end of the fourth part having the second, the third, and the fourth parts extended to the farthest position from the support column. Further, the minimum length of the beam will be the distance from the support column to the end of the first part having the second, the third, and the fourth parts fully retracted toward the side of the support column into the first beam. If a four-part extension beam is used, the length can be reduced more compared to a case where a three-part extension beam is used. Thus, while maintaining the maximum length, the beam length can be further reduced when it is retracted. Further, in this manner, although the entire size of the mobile radiation imaging apparatus is reduced, the operator can check the information displayed on the monitor 9 even when the radiation generation unit is at the home position. Even if the operator does not need to check the information of the monitor 9 while the operator is actually moving the mobile radiation imaging apparatus, it is convenient for the operator to be able to obtain information from the monitor 9 when, for example, the operator is waiting outside a hospital room or while another medical-care professional is positioning the patient even if the X-ray tube 1 is at the home position. Thus, the convenience of apparatus can be greatly enhanced while realizing down-sizing of the apparatus and maintaining the maximum length of the beam 3.

The support column 4 includes a movable support column 302 and an immovable support column 303. While the immovable support column 303 is immovably fixed to the cart portion 6, the movable support column 302 is fixed in an elevatable manner. The movable support column 302 supports the beam 3 via the beam-supporting unit 5. Thus, the movable support column 302 indirectly supports the X-ray tube 1. Further, the immovable support column 303 is rotatable around an axis, indicated by a dot-and-dash line illustrated in FIG. 3, by the support-column rotation unit 8. Since the movable support column 302 rotates according to the rotation of the immovable support column 303, the X-ray tube 1 rotates accordingly around the axis of the support column 4.

Since the support column 4 is extendable, when the support column 4 is contracted (e.g., the X-ray tube 1 is at the home position), the support column 4 is set to low height. If the support column 4 is set to low height, it can prevent obstruction of the view of the operator and the visibility ahead is improved. Together with the beam 3 including four parts or more, the support column 4 which is extendable contributes to greatly enhancing the visibility ahead of the mobile radiation imaging apparatus.

According to the example illustrated in FIG. 3, the guiding rod 10 does not necessarily protrude from the beam 3. Whether the beam 3 and the X-ray tube 1 are in the storage positions, which are the positions they are in when the apparatus is moved, may be detected by a magnet and a magneto-metric sensor provided on the guiding rod 10 and the guiding rod accepting unit 11 provided on the cart portion 6. Further, according to the apparatus illustrated in FIG. 3, when the X-ray tube 1 is moved from the storage position, the rotation of the rotation mechanisms 13 to 15 is stopped. Furthermore, all the motions of the apparatus may be stopped except for two motions (the movement of the beam-supporting unit 5 in the vertically upward direction along the support column 4 and the rotation of the support column 4 according to a brake release of the support column rotation unit 8).

According to an external view of the mobile radiation imaging apparatus of the exemplary embodiment illustrated in FIG. 4, components similar to those illustrated in FIG. 3 are denoted by the same reference numerals and their descriptions may not be repeated. The present embodiment is similar to the exemplary embodiment described with reference to FIG. 3, and the points different from those described with reference to FIG. 3 will be mainly described.

According to the example illustrated in FIG. 4, the recessed portion 300 includes a pair of wall members 401 which covers at least a portion of the two side faces of the X-ray tube 1 or the collimator 2 with respect to the forward moving direction 350. A storage space of the X-ray tube 1 or the collimator 2 is formed by the pair of wall members 401 and the recessed portion 300. The pair of wall members 401 may be formed integrally with the cart portion 6. Since the side faces of the X-ray tube 1 or the collimator 2 are covered by the pair of wall members 401, the possibility of the X-ray tube 1 or the collimator 2 receiving an external impact can be reduced.

Although the display face of the monitor 9 is arranged near a joint region of the collimator 2 and the X-ray tube 1 in the vertical direction according to the example illustrated in FIG. 3, the monitor 9 is positioned above the collimator 2 according to the example illustrated in FIG. 4. According to an exemplary embodiment, the weight of the X-ray tube 1 and the collimator 2 is approximately 30 kg and the height of the support column 4 when it is retracted is approximately 1.0 m to 1.5 m. Thus, for an adult having the body height of 1.6 m to 1.7 m, the view is not obstructed by the support column 4. Further, the position where the monitor 9 is arranged allows smaller difference in the line of sight when the operator looks forward in the forward moving direction 350. Further, since the monitor 9 is tilted by an angle of attack, the movement associated with the line of sight can be reduced.

Additionally, according to the example illustrated in FIG. 4, when the X-ray tube 1 is moved from the storage position, not only the rotation of each of the rotation mechanisms 13 to 15 is stopped but all the motions may be stopped except for the vertical movement of the beam supporting unit 5 with respect to the support column 4. Accordingly, the possibility of the X-ray tube 1 colliding with the monitor 9 is further reduced.

According to the above-described configuration, since the rotation of the X-ray tube 1 is inhibited when the operator moves the apparatus, the possibility of the X-ray tube 1 contacting the monitor 9 can be reduced. Thus, the operator can easily move the X-ray tube 1 from the storage position and the operability of the operator can be improved.

Figure 5:
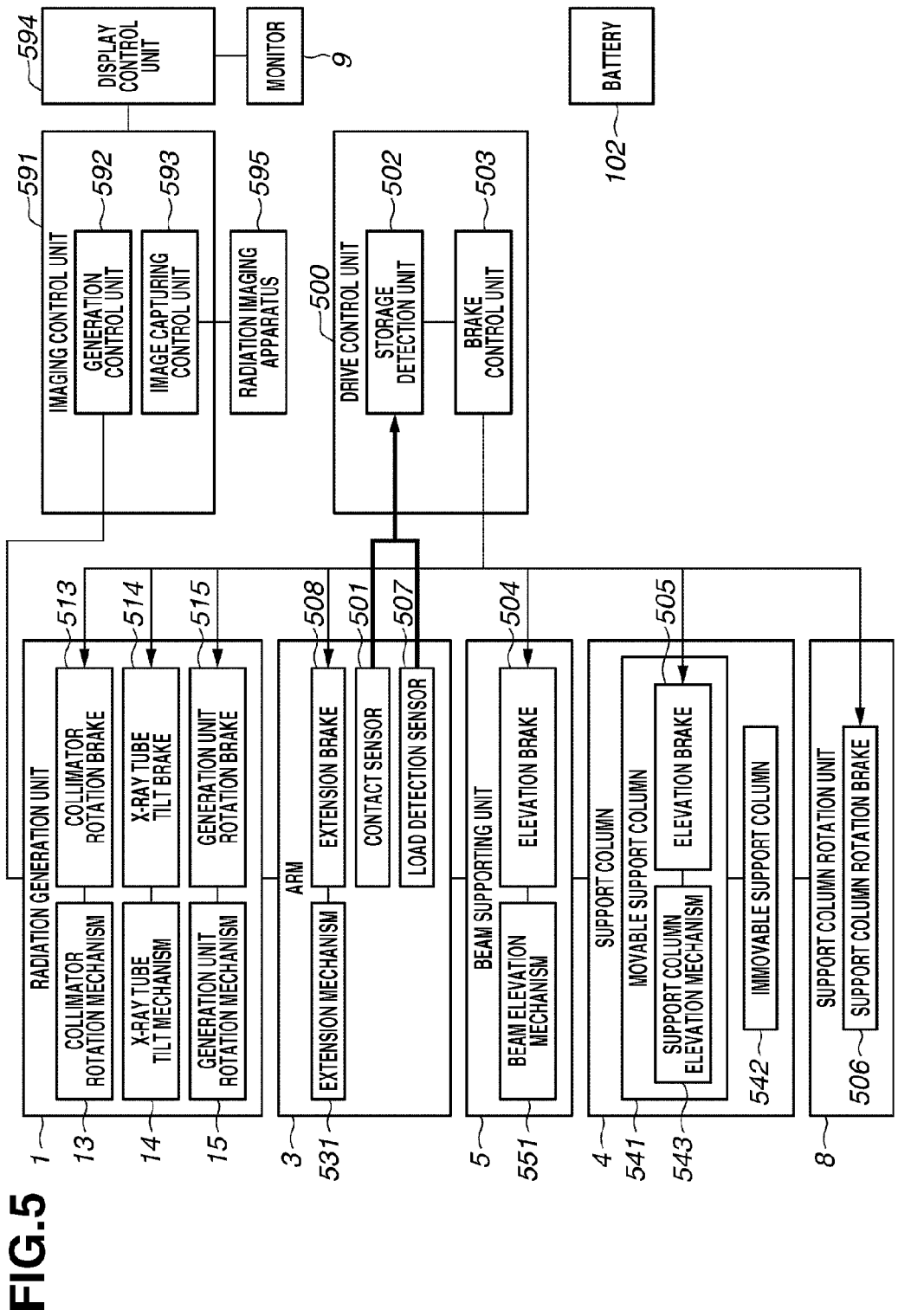
FIG. 5 is a block diagram of the mobile X-ray imaging apparatus according to an exemplary embodiment.

Next, the mobile radiation imaging apparatus according to the exemplary embodiment will be described with reference to FIG. 5 from the viewpoint of apparatus control. Since the components with the reference numerals same as those in FIG. 1 are similar to such components, their descriptions are not repeated.

On the beam 3, there are provided the radiation generation unit 1 (the X-ray tube 1), the collimator 2, and a load detection sensor 507 which detects the operational force which the beam 3 receives from the operator. Additionally, on the bottom face of the beam 3, there are provided a contact sensor 501 which detects contact with a particular member of the cart portion 6. The contact sensor 501 is, for example, a magnetometric sensor. The contact sensor 501 is arranged such that if, for example, the beam 3 including an extension mechanism 531 is extended from a non-imaging position, the contact sensor 501 comes close to or contacts a particular member of the cart portion 6. When the operator stores the beam 3, if the radiation generation unit 1 is tilted, the radiation generation unit 1 may contact other members of the apparatus such as the monitor 9. Thus, the beam 3 may be configured such that the beam 3 does not contact the cart portion 6 on such an occasion.

If the support column 4 is extendable, it includes a movable support column 541 and an immovable support column 542. A drive control unit 500 controls movement and motion of each setting member of the apparatus, determines the position of the radiation generation unit, and limits the motion of each setting member which sets the irradiated range of radiation. A storage detection unit 502 of the drive control unit 500 detects a signal sent from the contact sensor 501. On receiving a signal indicating the contact from the contact sensor 501, the storage detection unit 502 determines that the storage is completed. A brake control unit 503 outputs a signal by which each brake of the setting members is applied to each setting member.

A collimator rotation brake 513, an X-ray tube tilting brake 514, and a generation unit rotation brake 515 are provided on the collimator rotation mechanism 13 which rotates the collimator 2 of the radiation generation unit 1, the X-ray tube tilting mechanism 14 which tilts the X-ray tube 1, and the generation unit rotation mechanism 15 by which the X-ray tube 1 rotates around the axis of the support column 4, respectively. A deadman-type of brake can be used for the brakes 513 to 515.

An extension brake 508 which limits the extension of the beam 3 is provided for the extension mechanism 531 that extends the beam 3. The extension mechanism is, for example, a telescopic extension mechanism. An elevation brake 504, which limits the elevation of the beam-supporting unit 5, is provided on a beam elevation mechanism 551 provided for the elevation of the beam-supporting unit 5. The elevation brake 504 can be provided on the side of the support column 4.

An elevation brake 505 which limits the elevation of the movable support column 541 is provided on a support column elevation mechanism 543 for the movable support column 541. Further, a support-column rotation brake 506 which limits the rotation of the support column 4 is provided on the support column rotation unit 8.

If the X-ray tube 1 is at the storage position, the brakes are applied according to a signal output from the brake control unit 503. Thus, the motion and the movement of the mechanisms 13 to 15 are limited. If a deadman brake is employed, the brake will be applied in a de-energized state. Thus, the brake control unit 503 limits the motion by not performing the brake release control.

An imaging control unit 591, a display control unit 594, and the drive control unit 500 correspond to the control unit 101 illustrated in FIG. 1. The imaging control unit 591 includes a generation control unit 592, which controls the generation of radiation performed by the radiation generation unit 1, and an image-capturing control unit 593, which controls a radiation imaging apparatus 595. The radiation imaging apparatus 595 includes, for example, an X-ray image sensor and a reading unit. The X-ray image sensor includes an image sensor unit including a fluorescent material, which converts radiation to visible light, and a plurality of photoelectric conversion elements, which converts the visible light to an electric signal. The reading unit performs amplification and AD conversion of the electric signal and generates radiation image data. The radiation image data is transmitted to the imaging control unit 591 of the display control unit 594 in the mobile radiation imaging apparatus via a communication circuit of the radiation imaging apparatus 595 and displayed on the monitor 9 according to the control of the display control unit 594. The radiation imaging apparatus 595 is, for example, a cassette-type flat panel detector (FPD). A FPD that meets the purpose of the imaging is selected and the FPD is set to the mobile radiation imaging apparatus. The mobile radiation imaging apparatus and the radiation imaging apparatus may be called together as a mobile radiation imaging system.

Figure 6:
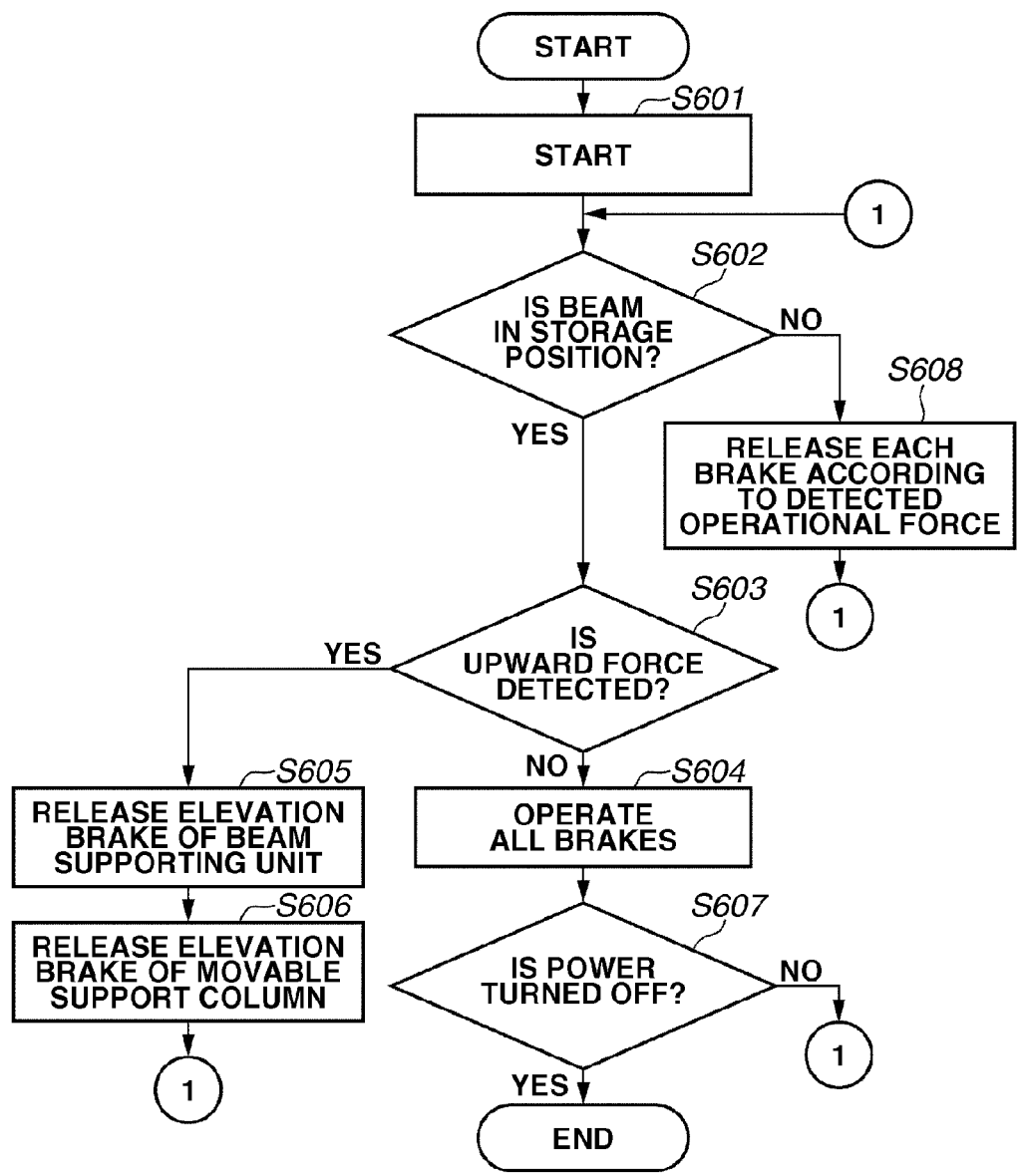
FIG. 6 is a flowchart illustrating control of the mobile X-ray imaging apparatus according to an exemplary embodiment.

FIG. 6 is a flowchart illustrating the control of the mobile radiation imaging apparatus according to the exemplary embodiment. In step S601, when the user presses, for example, a power button, power is supplied to each unit of the apparatus from the battery 102 and the mobile radiation imaging apparatus is started. In step S602, the drive control unit 500 determines whether the beam 3 is in the storage position. The drive control unit 500 makes the determination according to whether the storage detection unit 502 has detected a signal output from the contact sensor 501. If the drive control unit 500 determines that the radiation generation unit 1 is at the non-imaging position (storage position) (YES in step S602), the processing proceeds to step S603.

In step S603, the drive control unit 500 determines whether an upward force is applied to the beam 3 according to a signal obtained from the load detection sensor 507. If the drive control unit 500 determines an upward force and further determines that it is greater than a predetermined threshold value (YES in step S603), the processing proceeds to step S605. In step S605, the brake control unit 503 releases the elevation brake 504 of the beam-supporting unit 5. In step S606, the brake control unit 503 releases the elevation brake 505 of the movable support column 541. Thus, if an upward force is detected, the radiation generation unit 1 can be moved from the non-imaging position. The process returns to S602 thereafter. On the other hand, if an upward force is not detected in step S603 (NO in step S603), the processing proceeds to step S604. In step S604, the brake control unit 503 applies all brakes and limits the operation of each setting member. If the brakes are already applied, the application of the brakes is maintained by the brake control unit 503. If the beam is in the storage position, the elevation brakes 504 and 505 are not released unless an upward force is detected. In step S607, the control unit determines whether power is turned off. If the control unit determines that power is turned off (YES in step S607), the processing ends. If the control unit determines that power is not yet turned off (NO in step S607), the processing returns to step S602.

In step S602, if the drive control unit 500 determines that the radiation generation unit 1 is not at the storage position (NO in step S602), the processing proceeds to step S608. In step S608, the brake control unit 503 determines whether an operational force is applied according to a signal from the load detection sensor 507. If the brake control unit 503 determines that an operational force is applied, the brake control unit 503 releases each brake. If an assisting mechanism which includes, for example, a motor, is provided, the motor is driven according to the operational force. Accordingly, the user can move each setting member by a smaller force. Each setting member will be positioned according to the operation of the operator.

A configuration of the mobile X-ray imaging apparatus according to another exemplary embodiment of the present invention will be described with reference to FIG. 7. According to the present embodiment, a relative position of the X-ray tube and the monitor is detected and the application range of the present invention is broadened.

Figure 7:
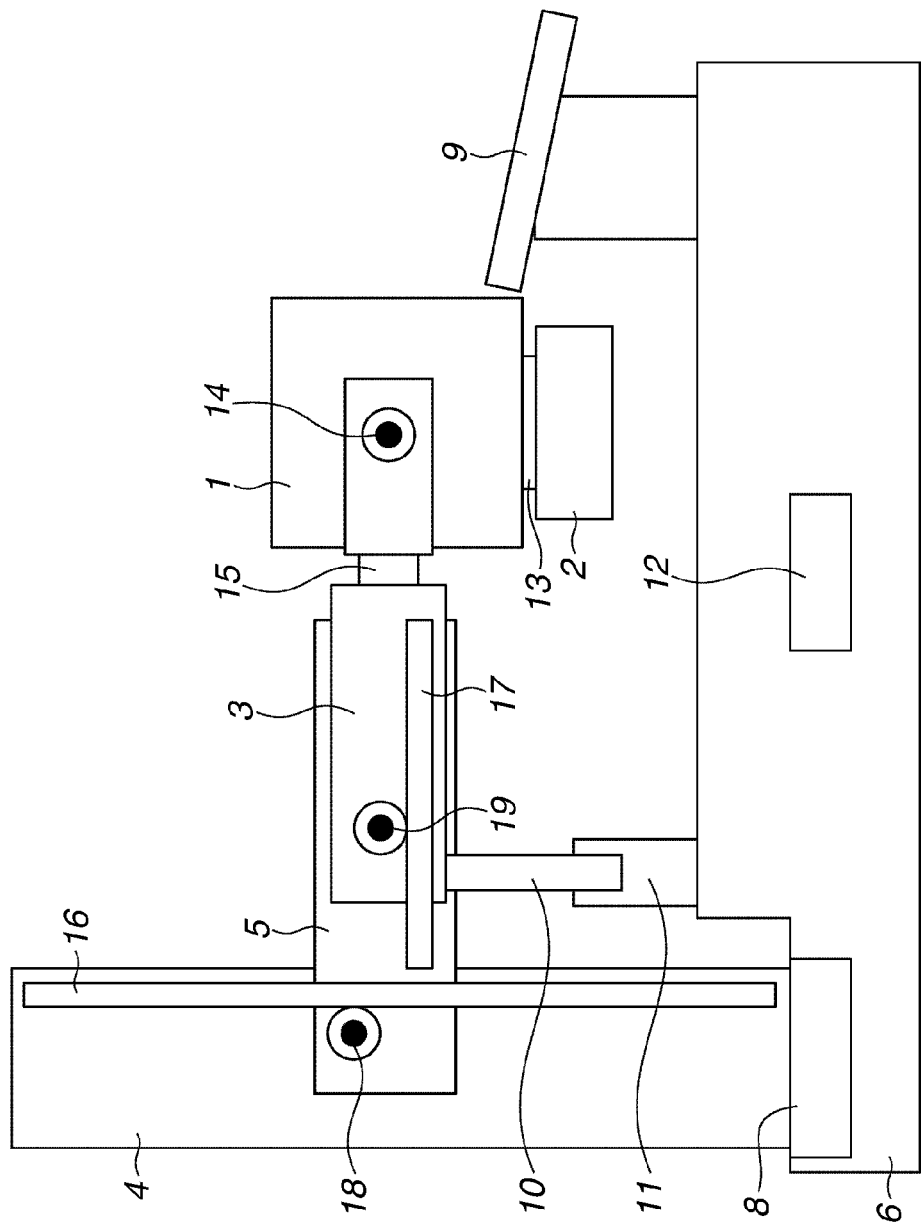
FIG. 7 illustrates another configuration of the X-ray imaging apparatus according to an exemplary embodiment.

In FIG. 7, the components denoted by the reference numerals 1 to 6 and 9 to 11 are similar to the components denoted by the same reference numerals in FIG. 1. The support-column rotation unit 8 is based on the support-column rotation unit 8 according to the first exemplary embodiment but further includes a rotational angle sensor which detects the rotational angle of the support column 4 with respect to the cart portion 6. A control unit 12 controls the drive of the entire apparatus. The collimator rotation mechanism 13, the X-ray tube tilting mechanism 14, and the generation-unit rotation mechanism 15 are based on the rotation mechanisms 13 to 15 according to the first exemplary embodiment but each of them further includes a rotational angle sensor used for detecting a rotational angle. The results of the rotational angle detection of the support-column rotation unit 8 and the rotation mechanisms 13 to 15 are sent to the control unit 12. The mobile X-ray imaging apparatus according to the present embodiment includes racks 16 and 17 and pinions 18 and 19. A rotational speed sensor is provided to each of the pinions 18 and 19. The result detected by each rotational speed sensor is sent to the control unit 12. The control unit 12 calculates the position of the pinion on the rack based on the number of turns of the pinion. In other words, if the beam-supporting unit 5 is moved along the support column 4, the position of the beam supporting unit 5 can be calculated according to the rotation and the movement of the pinion 18 in the beam supporting unit 5 on the rack 16 in the support column 4. Further, if the beam 3 is moved in the horizontal direction, the position of the beam 3 can be calculated according to the rotation and the movement of the pinion 19 in the beam 3 on the rack 17 in the beam-supporting unit 5. Further, since the beam 3 is connected to the X-ray tube 1 via the generation-unit rotation mechanism 15, the relative position of the X-ray tube 1 and the cart portion 6 can be calculated according to the result of the rotational angle detection transmitted to the control unit 12. In other words, since the monitor 9 is fixed to the cart portion 6, the control unit 12 can calculate the relative position of the monitor 9 and the X-ray tube 1. Although a one-stage extending type beam by the beam 3 and the beam-supporting unit 5 is illustrated in FIG. 7, the beam can include more parts. If the beam includes more parts, a rack and pinion corresponding to the number of parts in the beam and a rotational speed sensor of a level similar to the sensor used for the pinions 18 and 19 can be used. Further, in order to obtain stable rotation of the pinion, a linear guide may be provided between the support column 4 and the beam-supporting unit 5 or between the beam supporting unit 5 and the beam 3. If an acceleration sensor is provided in the X-ray tube 1, the relative position of the X-ray tube 1 from the storage position can be obtained according to calculation of the amount of movement of the X-ray tube 1 from the detection result of the acceleration sensor. Further, if a 3-dimensional position sensor for example a sensor provided by POLYHEMUS Inc., is provided on each of the X-ray tube 1 and the monitor 9, the relative position can be obtained from each absolute position. The control unit 12 includes a rotational angle table. The rotational angle table includes relative positions of the X-ray tube 1 and the monitor 9 when they are in a non-contact state with respect to the rotation of each of the rotation mechanisms 13 to 15. In this manner, even if the X-ray tube 1 is moved from the storage position, which is the position where the X-ray tube 1 is when the operator moves the apparatus, since the rotation of the rotation mechanisms 13 to 15 is limited according to the relative position of the X-ray tube 1 and the monitor 9, the contact of the X-ray tube 1 and the monitor 9 can be avoided.

Figure 8:
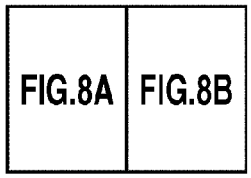
FIG. 8, which is composed of FIGS. 8A and 8b, is another block diagram of the mobile X-ray imaging apparatus according to an exemplary embodiment.
Figure 8A:
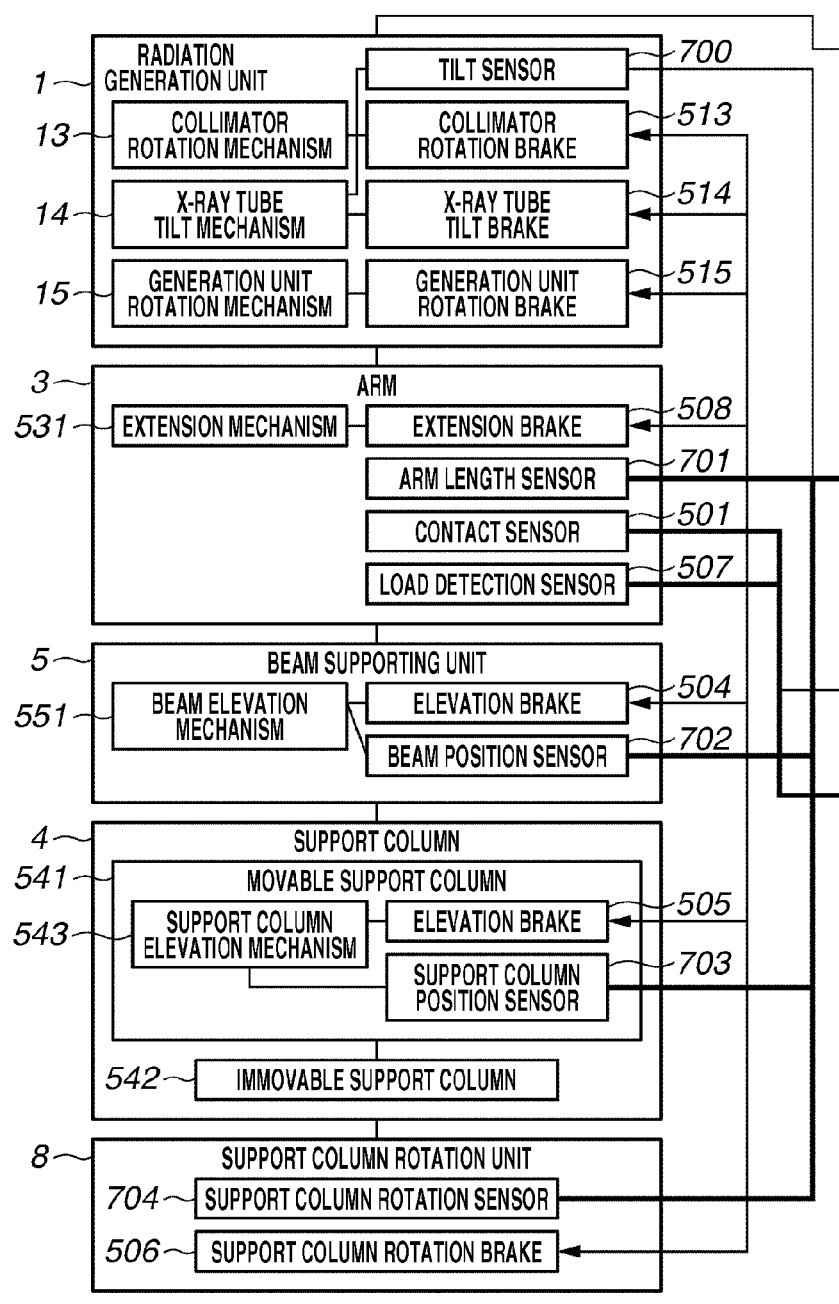
Figure 8B:
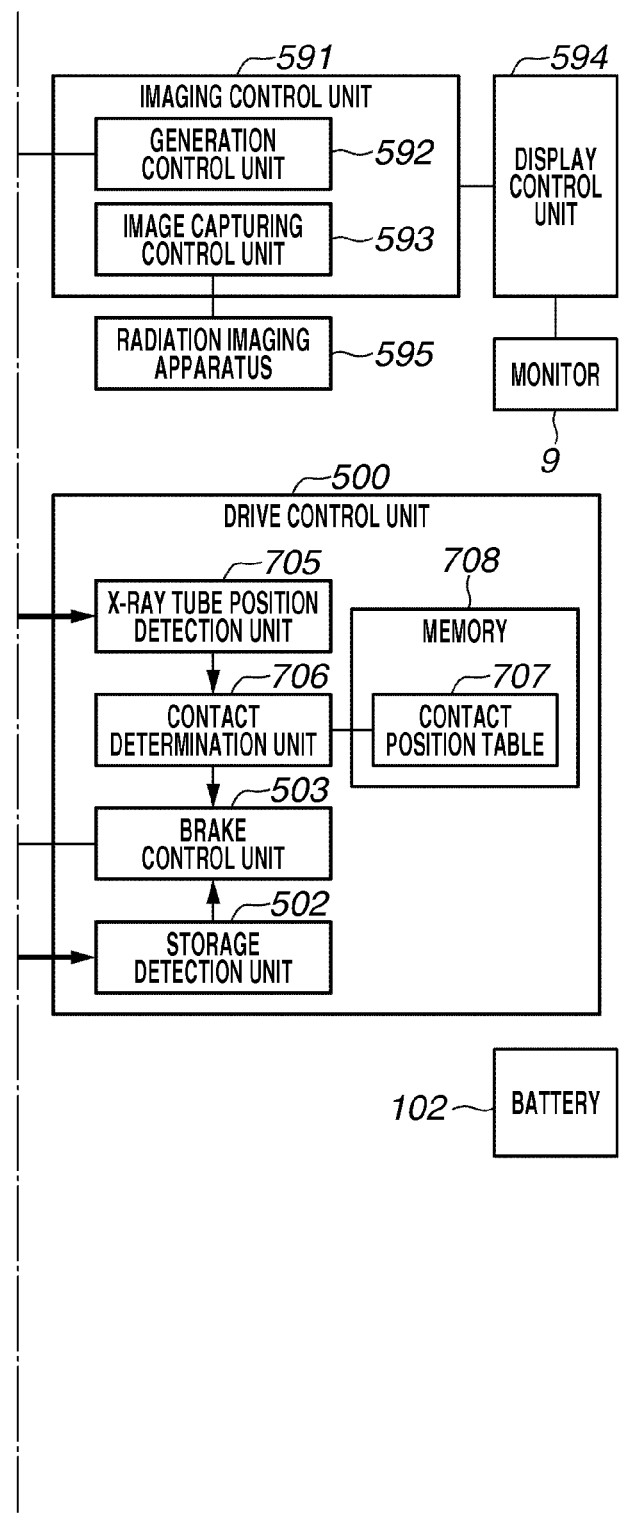

Next, the mobile radiation imaging apparatus according to the exemplary embodiment will be described mainly from the viewpoint of apparatus control with reference to FIG. 8, which is composed of FIGS. 8A and 8b. Since the components denoted by the reference numerals same as those in the illustrations above are similar components, their descriptions are not repeated.

On the radiation generation unit 1, the beam 3, the beam supporting unit 5, the support column 4, and the support column rotation unit 8, there are provided a tilt sensor 700, a beam length sensor 701, a beam position sensor 702, a support column position sensor 703, and a support column rotation sensor 704, respectively. The tilt sensor 700 detects the tilt state by the X-ray tube tilting mechanism 14 of the radiation generation unit 1. The beam length sensor 701 detects the extended state of the beam 3, which holds the radiation generation unit 1. The beam position sensor 702 detects the elevation state of the beam 3, which holds the radiation generation unit 1 with respect to the support column 4. The support-column position sensor 703 detects the extended state of the support column 4, which indirectly holds the radiation generation unit 1. The support-column rotation sensor 704 detects the rotation state of the support column 4, which indirectly holds the radiation generation unit 1. The position and orientation states of these setting members are detected by the above-described sensors. Additionally, a sensor which detects a rotation state of the collimator 2 included in the setting members and a sensor which detects a rotation state of the radiation generation unit 1 may be provided. Output of these sensors is input in an X-ray tube position detection unit 705 of the drive control unit 500. The X-ray-tube position detection unit 705 determines the position and orientation of the radiation-generation unit 1 based on the input from the sensors. A contact determination unit 706 determines whether the radiation-generation unit 1, the collimator 2, or the beam 3 contacts other members of the mobile radiation imaging apparatus by referencing a contact position table 707 stored in a memory 708. The contact position table 707 stores information regarding the output values of each sensor when the setting members contact other members of the mobile radiation imaging apparatus. The table is experimentally generated based on the relation between the size and the arrangement of each setting member and each member of the mobile radiation generating apparatus.

Further, according to another example, the contact determination unit 706 determines whether the radiation generation unit 1 contacts each member of the mobile radiation generating apparatus by using a three-dimensional structure model of the entire mobile radiation generating apparatus including the radiation generation unit 1, the beam 3, and the support column 4. The three-dimensional structure model is stored in the memory 708. The brake control unit 503 controls each motion of the brakes of the setting members which require limited motions according to the determination result of the contact. Thus, the impact on the members can be reduced.

Figure 9:
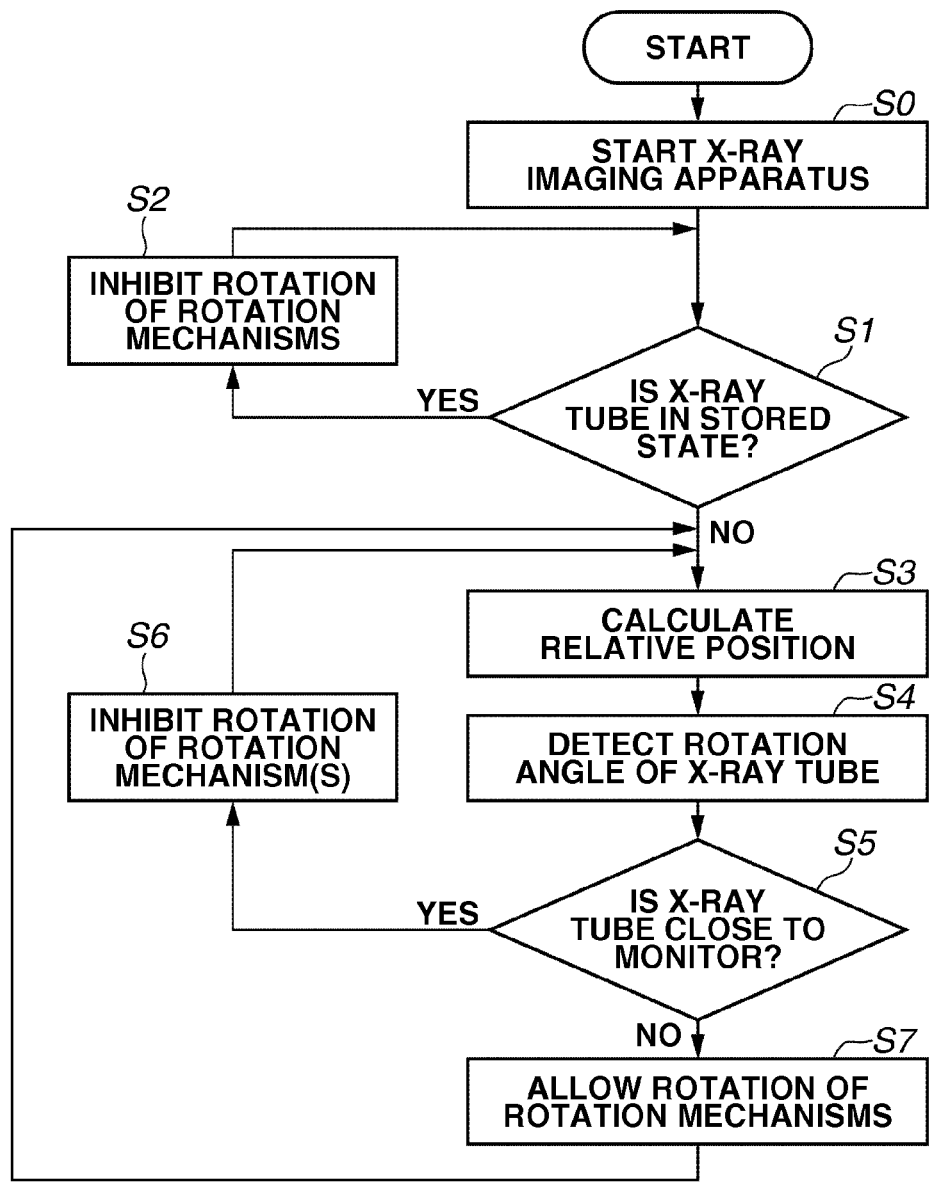
FIG. 9 is a flowchart illustrating another control according to an exemplary embodiment.
Figure 10A:
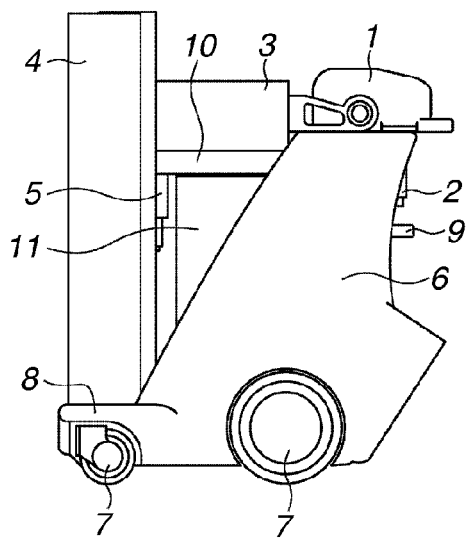
FIGS. 10A, 10B, 10C, and 10D illustrate another external view of the mobile X-ray imaging apparatus according to an exemplary embodiment.
Figure 10B:
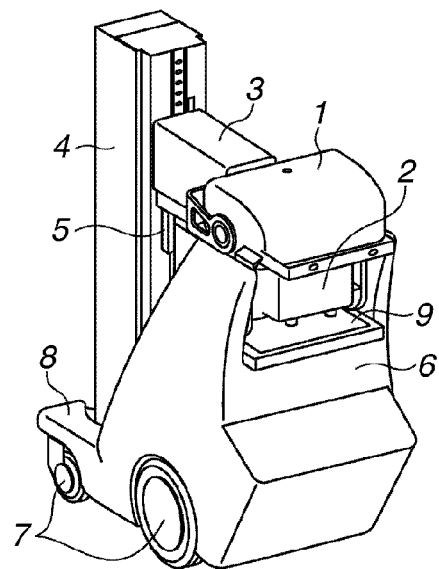
Figure 10C:
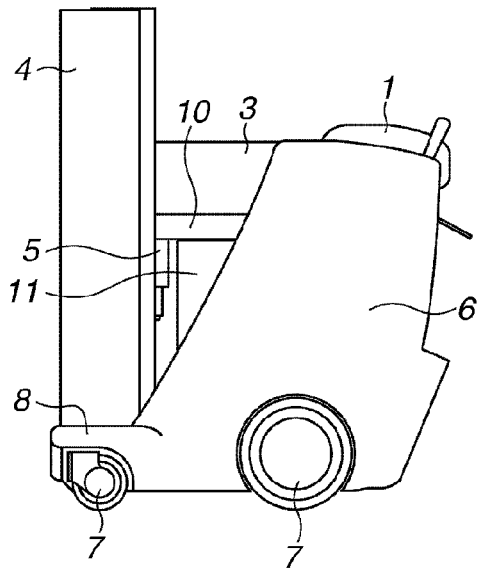
Figure 10D:
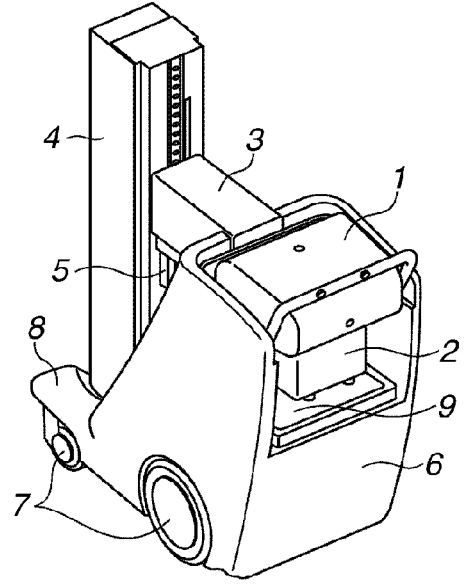

FIG. 9 is a flowchart illustrating a system according to the above-described exemplary embodiment. In step S0, when the operator presses a power switch, the control unit 12 starts the mobile radiation generating apparatus. In step S1, according to the detection result of the contact sensor of the guiding rod 10 or the guiding rod-accepting unit 11, the control unit 12 determines whether the X-ray tube 1 is in the storage position. If the X-ray tube 1 is in the storage position (YES in step S1), the processing proceeds to step S2. If the X-ray tube 1 is not in the storage position (NO in step S1), the processing proceeds to step S3. In step S2, the control unit 12 inhibits the rotation of the rotation mechanisms 13 to 15. In step S3, the control unit 12 calculates a relative position of the X-ray tube 1 and the monitor 9 from the detection result of each rotational angle sensor. In step S4, the control unit 12 detects the direction the X-ray tube 1 is facing according to the rotational angle sensor of the rotation mechanisms 13 to 15. In step S5, based on the information obtained in steps S3 and S4, the control unit 12 determines whether the X-ray tube 1 is close to the monitor 9 by referencing the rotational angle table including the non-contact information of the X-ray tube 1 and the monitor 9. Whether the X-ray tube 1 is close to the monitor 9 is mainly determined according to the sampling time of the control, the apparatus shape, and the rotation speed of the X-ray tube 1. If it is determined that the X-ray tube 1 is close to the monitor 9 (YES in step S5), the processing proceeds to step S6. If it is determined that the X-ray tube 1 is not close to the monitor 9 (NO in step S5), the processing proceeds to step S7. In step S6, the control unit 12 inhibits the rotation of any or all of the rotation mechanisms 13 to 15 which is determined as causing the close state of the X-ray tube 1 and the monitor 9 determined in step S5. As for the rotation mechanism not determined as causing the close state of the X-ray tube 1 and the monitor 9 determined in step S5, the control unit 12 allows the rotation. In step S7, the control unit 12 allows the rotation of all the rotation mechanisms 13 to 15. Then, the processing returns to step S3.

In step S6, the control unit 12 can inhibit rotation of all the rotation mechanisms 13 to 15. In this manner, the operator can clearly understand that the rotation of the X-ray tube 1 is inhibited and thus gives a high priority to moving the position of the X-ray tube 1. Further, the inhibition of rotation may be released after the elapse of a predetermined length of time after step S6.

According to the above-described configuration, when the operator rotates the X-ray tube, the possibility of the X-ray tube contacting the monitor can be reduced and a mobile X-ray imaging apparatus with improved operability can be realized.

FIGS. 10A, 10B, 10C, and 10D illustrate another configuration of the mobile radiation generating apparatus according to an exemplary embodiment. According to the example illustrated in FIGS. 10A, 10B, 10C, and 10D, the X-ray tube 1 is stored above the monitor 9. When the X-ray tube 1 is stored, a wall for blocking radiation exposure protrudes from the cart portion 6. The monitor 9 is slidably supported by a pair of guide rails. According to the guide rails, the monitor 9 can be easily taken out from where it is stored under the X-ray tube 1 when the operator desires to check information. According to the example illustrated in FIGS. 10A, 10B, 10C, and 10D, the guiding rod 10 does not necessarily protrude from the beam 3. By a magnet and a magnetometric sensor of the guiding rod 10 and the guiding rod-accepting unit 11 provided on the cart portion 6, whether the beam 3 and the X-ray tube 1 are in the storage positions, which are the positions they are in when the operator moves the apparatus, can be detected. Further, according to the apparatus illustrated in FIGS. 10A, 10B, 10C, and 10D, when the operator moves the X-ray tube 1 from the storage position, the control unit 12 may not only inhibit the rotation of the rotation mechanisms 13 to 15 but inhibit all motions other than the vertical movement of the beam supporting unit 5 with respect to the support column 4 and the extending movement of the beam 3. The extension of the beam 3 can be stopped by an extended position fixing unit of the beam 3. Further, if a rotational angle table including non-contact information of the X-ray tube 1 and the wall of the cart portion 6 for preventing radiation exposure is provided, the control unit 12 can add determination processing of whether the X-ray tube 1 is close to the wall of the cart portion 6 for preventing radiation exposure to step S5 in FIG. 9. Then, not only the contact of the X-ray tube 1 with the monitor 9 is prevented but the contact with the wall of the cart portion 6 for preventing radiation exposure can also be prevented.

According to the above-described configuration, when the operator arranges the position of the X-ray tube 1, the contact of the X-ray tube 1 with the monitor 9 can be prevented and a mobile X-ray imaging apparatus with improved operability can be realized.

Figure 11:
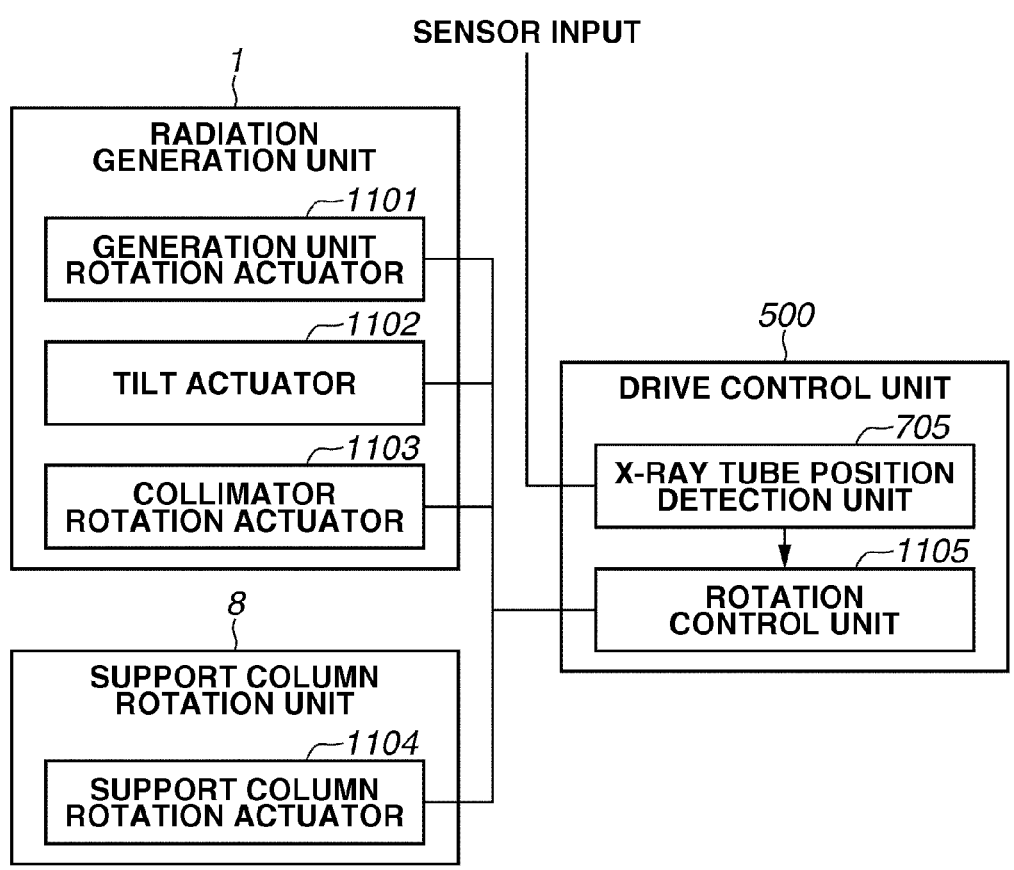
FIG. 11 is another block diagram of the mobile X-ray imaging apparatus according to an exemplary embodiment.

A mobile radiation imaging apparatus according to another exemplary embodiment will be described with reference to FIG. 11. According to the present embodiment, each of the rotation mechanisms of the X-ray tube 1 includes an actuator which includes a motor, and the application range of the present invention is broadened. According to the present embodiment, a generation-unit rotation actuator 1101, a tilt actuator 1102, and a collimator rotation actuator 1103 are provided on the rotation mechanisms 13, 14, and 15, respectively. The actuators 1101 to 1103 are controlled by a rotation control unit 1105 of the drive control unit 500. Further, a support column rotation actuator 1104 can be provided on the support column rotation unit 8. According to the above-described configuration, rotation power transmission mechanisms that transmit rotation power from the motor are provided in the rotation mechanisms 13 to 15. According to the drive of each motor, the X-ray tube 1 can be moved to an arbitrary direction. Further, if the operator desires not to use each motor, the motor is de-energized by the rotation control unit 1105. Then, the operator can manually move the X-ray tube 1.

Figure 12:
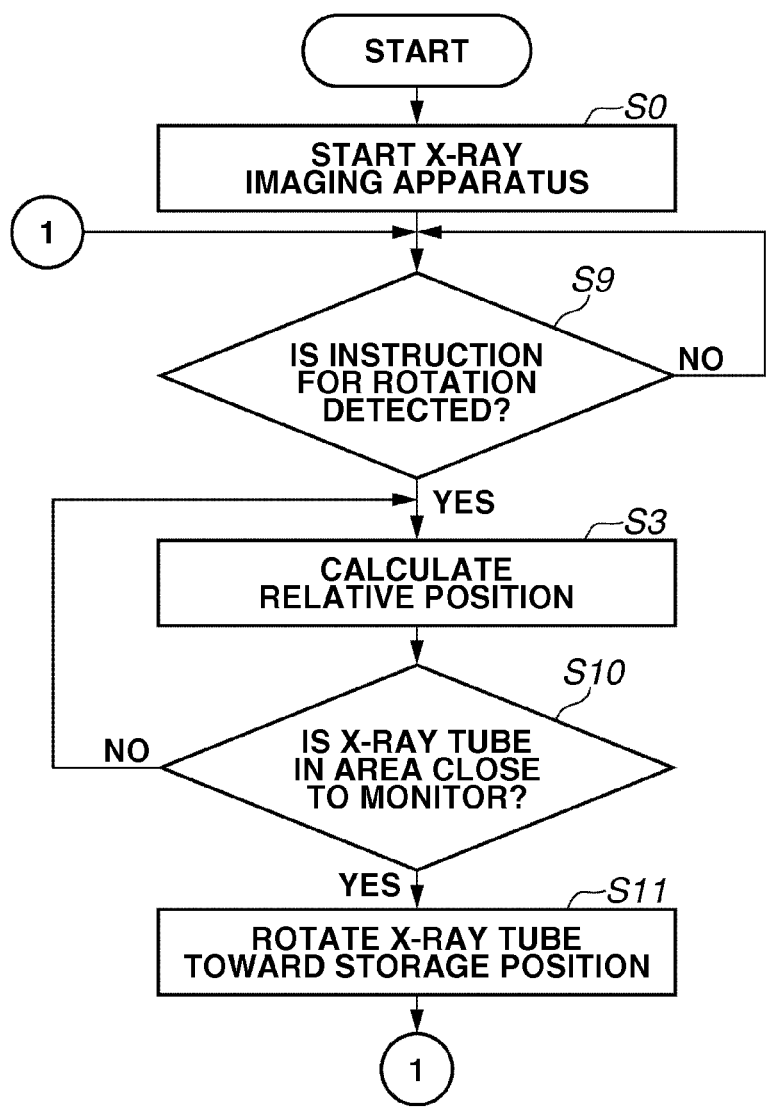
FIG. 12 is a flowchart illustrating another control of an exemplary embodiment.

FIG. 12 is a flowchart illustrating a system according to a third exemplary embodiment of the present invention. In step S9, the control unit 12 determines whether the rotation of the X-ray tube 1 is instructed. For example, if instruction buttons corresponding to the rotation of the rotation mechanisms 13 to 15 of the X-ray tube 1 are provided on an operation unit (not illustrated), and if the drive control unit 500 determines that one of the buttons has been pressed, the control unit 12 determines that the rotation has been instructed. In step S9, if the control unit 12 determines that the rotation has been instructed (YES in step S9), the processing proceeds to step S3. If the control unit 12 determines that the rotation has not yet been instructed (NO in step S9), the processing returns to step S9.

In step S3, the control unit 12 calculates a relative position of the X-ray tube 1 and the monitor 9 from the detection result of each rotational angle sensor. In step S10, the control unit 12 determines whether the X-ray tube 1 is in an area close to the monitor 9 from the information obtained in step S3 and the rotational angle table including the non-contact information of the X-ray tube 1 and the monitor 9. If the X-ray tube 1 is not in such an area (NO in step S10), the processing returns to step S3. If the X-ray tube 1 is in such an area (YES in step S10), the processing proceeds to step S11. In step S11, the control unit 12 controls the rotation mechanisms 13 to 15 and rotates the X-ray tube 1 so that the X-ray tube 1 is turned in the direction of the X-ray tube 1 in the storage position. Before the control unit 12 moves the X-ray tube 1 to the storage position, the control unit 12 rotates the X-ray tube 1 until at least the X-ray tube 1 reaches a position where the X-ray tube 1 does not contact the monitor 9 by referencing the rotational angle table including the non-contact information of the X-ray tube 1 and the monitor 9.

According to the above-described configuration, the contact of the X-ray tube and the monitor can be avoided when the X-ray tube is moved to the storage position and the operability of the X-ray tube is improved.

Figure 13:
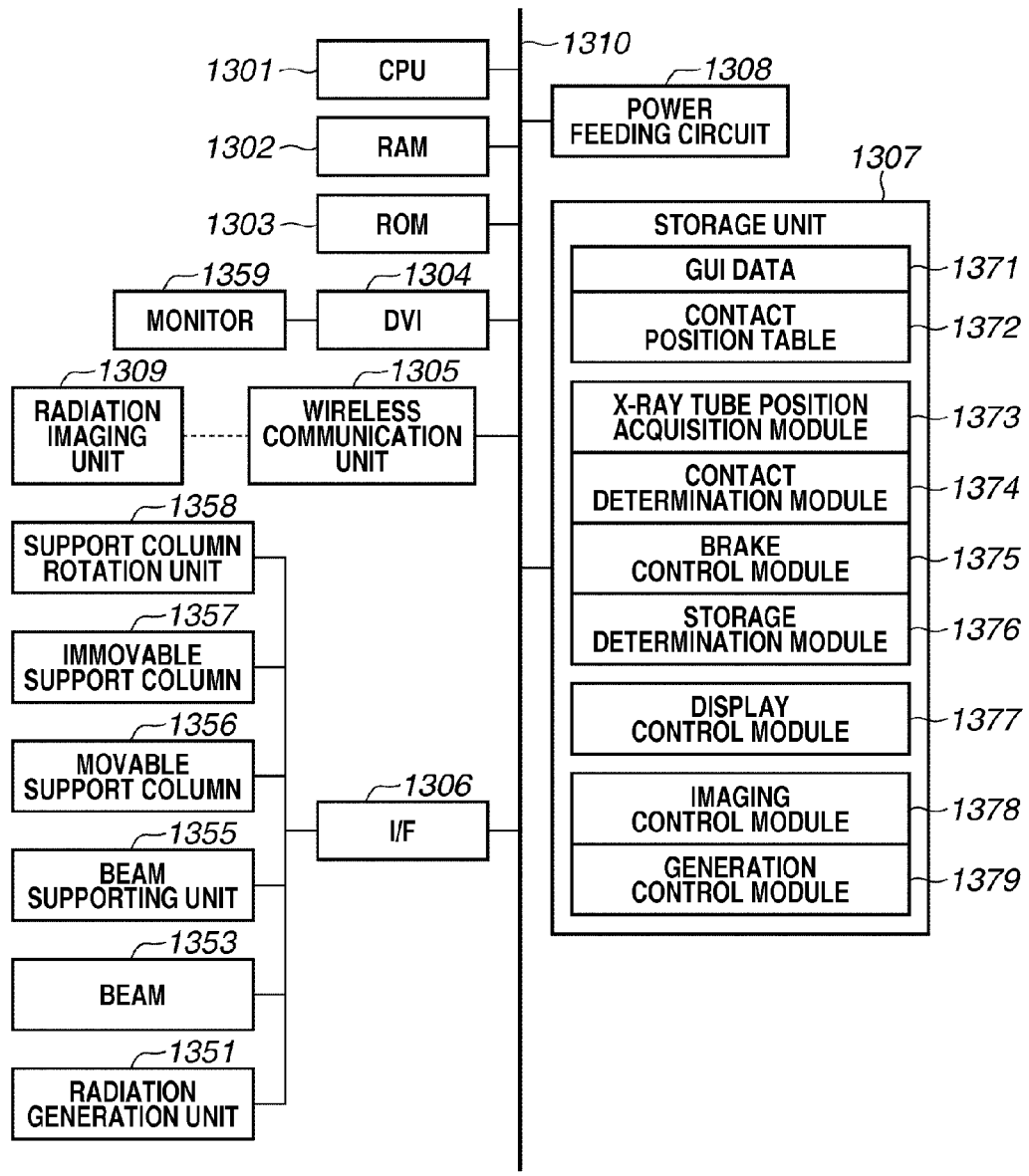
FIG. 13 is a block diagram illustrating another configuration example of a control unit according to an exemplary embodiment.

FIG. 13 illustrates the mobile radiation imaging apparatus using hardware and software of an electronic computer according to an exemplary embodiment. According to the present embodiment, a control unit of the mobile radiation generating apparatus includes a central processing unit (CPU) 1301, a random access memory (RAM) 1302, a read-only memory (ROM) 1303, a digital visual interface (DVI) 1304 as an interface with a monitor, a wireless communication unit 1305, an interface (I/F) 1306 as an interface with each of the setting members of the apparatus, a storage unit 1307, and a power feeding circuit 1308. The units shown above are connected with an internal bus 1310. The DVI 1304 is connected to a monitor 1359. The wireless communication unit 1305 communicates with a radiation-imaging unit 1309 by wireless communication. The I/F 1306 is connected to a support column rotation unit 1358, an immovable support column 1357, a movable support column 1356, a beam supporting unit 1355, a beam 1353, and a radiation generation unit 1351. The structures and functions of these units are similar to those of the above-described exemplary embodiment. In addition to graphical user interface (GUI) data 1371 displayed on the monitor 1359 and a contact position table 1372, various software programs are stored in the storage unit 1307. Such programs are an X-ray tube position acquisition module 1373, a contact determination module 1374, a brake control module 1375, a storage determination module 1376, a display control module 1377, an imaging control module 1378, and a generation control module 1379. These modules functions as an X-ray tube position detection unit, a contact determination unit, a brake control unit, a storage detection unit, a display control unit, an imaging control unit, and a generation control unit according to the above-described exemplary embodiment, respectively. The CPU 1301 loads the programs into the RAM 1302 and executes the programs. Accordingly, the control illustrated in the flowcharts in FIGS. 6, 9, and 12 is realized. Further, a rotation control module including the function of the rotation control unit 1105 illustrated in FIG. 11 may be stored in the storage unit 1307 in a computer-executable manner.

An apparatus realized by combining and changing the functions described in the above-described exemplary embodiments as appropriate is also included in the exemplary embodiments of the present invention. For example, regarding a mobile X-ray generating apparatus including the X-ray tube 1 which emits radiation, the collimator 2 arranged in the X-ray emitting direction of the X-ray tube 1 and limits the X-ray emission area, the beam 3 which holds the X-ray tube 1, the support column 4 which allows movement of the beam 3 in the vertical direction, the cart portion 6 which is a movable unit that supports the support column 4, and the monitor 9 on the upper face of the cart portion 6, the X-ray tube 1 includes the rotation mechanisms 14 and 15 which can rotate the X-ray tube 1 at least around two axes so that the direction of the X-ray emission can be changed, and the collimator 2 includes the rotation mechanism 13 which can rotate the X-ray tube 1 around an axis being the center of the X-ray emission, and if the X-ray tube 1 is in the storage position where the X-ray tube 1 is in when the apparatus is moving, the control unit 101 can control the rotation mechanisms 13 to 15 so that the rotation by the rotation mechanisms can be inhibited. The X-ray tube 1 includes the sensors 700 to 704 which detect the relative position of the X-ray tube 1 and the monitor 9, and the drive control unit 500 allows the rotation of all the rotation mechanisms 13 to 15 according to the detection results of the sensors 700 to 704. Further, each of the rotation mechanisms 13 to 15 includes a sensor which detects a rotational angle, and according to the detection results of the relative position detection sensors and the rotational angle sensor of the X-ray tube 1 and the monitor 9, the rotation mechanisms 13 to 15 can be controlled so that each rotation of the mechanisms can be independently inhibited. Further, the rotation mechanisms 13 to 15 further include the actuators 1101 to 1103 which allow automatic rotation, and according to the detection results of the relative position detection sensors and the rotational angle sensor of the X-ray tube 1 and the monitor 9, each of the rotation mechanisms 13 to 15 is independently rotated so that the direction of X-ray emission is changed.

Further, for example, although the operation of the rotation mechanisms 13 to 15 is controlled according to the operator pressing the instruction button, a switch may be provided for each of the above-described setting members or the supporting members. According to an exemplary embodiment, one switch is provided for each of the supporting members. According to another exemplary embodiment, in addition to the switch or in place of the switch, a switch is provided for each of the plurality of supporting members or all of the supporting members. The brake control unit 503 of the drive control unit 500 releases the limit of the motion of the supporting members when the switch is turned on. Further, if the X-ray tube 1 is detected in the storage position by the storage detection unit 502, the brake control unit 503 does not release the limit of the motion of some of the supporting members even if the switch is turned on. To be more precise, the movement of the X-ray tube 1 other than the upward movement in the vertical direction, in other words, downward and sideways movements, is limited. In this manner, since the supporting members will not be moved unless the switch is pressed, safety can be improved.

Further, by providing not only one switch but a plurality of switches, the possibility of the operator inadvertently pressing a switch can be reduced. Thus, the possibility of unintended movement of the supporting member can be reduced and safety can be enhanced.

Additionally, although the mobile radiation generating apparatus is described as an X-ray imaging apparatus according to the examples described above, the present invention is not limited to such an apparatus, and an imaging apparatus using other type of radiation is also included in the exemplary embodiment of the present invention.

Further, the mobile imaging apparatus is not limited to the apparatus described above. The mobile imaging apparatus can be an apparatus having one function out of beam extending function, beam elevating function, and support column extending and rotating function.

According to the above-described example, although the support column is described as extending in the vertical direction and the beam is described as a beam member that extends in the horizontal direction, each of the support column and the beam can extend in a first direction and a second direction different from the first direction.

The non-imaging position (storage position) is not limited to the above-described example and a plurality of non-imaging positions, ranges, or areas can exist.

Although a rotating anode X-ray tube with reflection target can be used for the X-ray tube 1, a fixed anode X-ray tube with transmission target can also be used for the radiation generation unit. If such an X-ray tube is used, since the mechanism for the rotating anode will be unnecessary, the size of the radiation generation unit can be reduced. Further, since the requirement for the load resistance of the supporting structure is reduced, the beam 3 and the support column 4 can be made thinner and more compact. Further, at least the manufacturing cost of the structures other than the radiation generation unit can be reduced.

According to the exemplary embodiments of the present invention, the possibility of the X-ray tube colliding with a monitor or other members in the vicinity when the X-ray tube is moved is reduced and operability can be improved.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-215966 filed Sep. 28, 2012, which is hereby incorporated by reference herein in its entirety.

What is claimed is:

1. A mobile radiation imaging apparatus comprising:
a radiation generation unit configured to generate radiation;
a cart;
a supporting member formed on the cart and including an arm which holds the radiation generation unit and is extendable in a horizontal direction;
a detection unit configured to detect arrangement of the radiation generation unit at a storage position;
a control unit configured to limit a motion of the supporting member according to a detection result by the detection unit; and
a monitor provided on an upper face side of the cart,
wherein, when arrangement of the radiation generation unit at the storage position is detected by the detection unit, the control unit limits an extension motion of the arm in the horizontal direction while simultaneously allowing an upward motion of the arm in a vertical direction.

2. The mobile radiation imaging apparatus according to claim 1, wherein the supporting member includes a collimator configured to limit an irradiated range by the radiation generation unit, and
wherein the control unit limits rotation of the collimator in an emission direction.

3. The mobile radiation imaging apparatus according to claim 1, wherein the supporting member includes a rotation mechanism configured to rotate the radiation generation unit, and
wherein the control unit limits rotation of the radiation generation unit by the rotation mechanism.

4. The mobile radiation imaging apparatus according to claim 1, wherein the supporting member includes a tilt mechanism configured to tilt the radiation generation unit, and
wherein the control unit limits tilting of the radiation generation unit by the tilt mechanism.

5. The mobile radiation imaging apparatus according to claim 1, wherein the arm includes a base portion and a moving portion, of a nesting type, which is movably connected to the base portion, and
wherein the moving portion includes three parts or more.

6. The mobile radiation imaging apparatus according to claim 1, wherein the supporting member further includes a support column unit which holds the arm in an elevatable manner, and
wherein the control unit limits a movement of the arm from the support column unit.

7. The mobile radiation imaging apparatus according to claim 1, wherein the supporting member further includes a support column unit which is extendable and holds the arm, and
wherein the control unit limits extension of the support column unit.

8. The mobile radiation imaging apparatus according to claim 7, wherein, if the radiation generation unit is arranged at the storage position, the control unit allows extension of the support column unit and limits contraction of the support column unit.

9. The mobile radiation imaging apparatus according to claim 1, wherein the supporting member includes a support column unit which is rotatable and indirectly holds the radiation generation unit, and
wherein the control unit limits rotation of the support column unit.

10. The mobile radiation imaging apparatus according to claim 1, further comprising an identification unit configured to identify a position of the radiation generation unit based on detection information of a position and orientation of the supporting member.

11. The mobile radiation imaging apparatus according to claim 1, wherein the detection unit obtains detection of arrangement of the radiation generation unit from at least any one of a sensor which detects a rotation state of a collimator included in the supporting member, a sensor which detects a rotation state of the radiation generation unit, a sensor which detects a tilt state by a tilt mechanism of the radiation generation unit, a sensor which detects an extended state of the arm, a sensor which detects an elevation state of the arm with respect to a support column unit, a sensor which detects an extended state of the support column unit which indirectly holds the radiation generation unit, and a sensor which detects a rotation state of the support column unit which indirectly holds the radiation generation unit.

12. The mobile radiation imaging apparatus according to claim 1, further comprising a motion limiting member of a deadman lock type, which acts on the supporting member, and
wherein the control unit limits motion of the supporting member by controlling the motion limiting member in a state where power is supplied to the mobile radiation imaging apparatus.

13. The mobile radiation imaging apparatus according to claim 1, further comprising a determination unit configured to determine contact of the radiation generation unit with another member of the mobile radiation imaging apparatus,
wherein the control unit limits motion of the supporting member according to a result of determination by the determination unit.

14. The mobile radiation imaging apparatus according to claim 1, wherein the supporting member includes a support column unit which is rotatable and holds the arm, and
wherein the control unit allows rotating motion of the support column unit when the radiation generation unit is in the non imaging at the storage position.

15. The mobile radiation imaging apparatus according to claim 1, further comprising a protruding portion configured to protrude in an emission direction from an emission face of a collimator of the radiation generation unit,
wherein the protruding portion contacts the radiation imaging apparatus at the storage position.

16. The mobile radiation imaging apparatus according to claim 1, further comprising a handle unit which extends in a position in an emission direction away from an emission face of a collimator of the radiation generation unit.

17. The mobile radiation imaging apparatus according to claim 16, wherein the handle unit is exposed at the storage position.

18. The mobile radiation imaging apparatus according to claim 1, further comprising a storage portion having a wall which covers at least one side face of at least the radiation generation unit or a collimator at the storage position.

19. The mobile radiation imaging apparatus according to claim 1, wherein, at the storage position, the monitor is arranged above a collimator of the radiation generation unit.

20. The mobile radiation imaging apparatus according to claim 1, further comprising:
a guide rail which movably holds the monitor in a slidable manner.

21. The mobile radiation imaging apparatus according to claim 1, wherein the storage position is at least one of a position determined as a position of the radiation generation unit when the mobile radiation imaging apparatus moves, a position of the radiation generation unit where the mobile radiation imaging apparatus is within an irradiated range, and a position where generation of radiation by the radiation generation unit is limited.

22. The mobile radiation imaging apparatus according to claim 1, further comprising a switch,
wherein the control unit releases a motion limit of the supporting member in response to the switch being turned on, and
wherein, if the arrangement of the radiation generation unit at the storage position is detected by the detection unit, the control unit does not release part of the motion limit of the supporting member even when the switch is turned on.

23. A mobile radiation imaging system comprising:
the mobile radiation imaging apparatus according to claim 1; and
an imaging apparatus including an X-ray image sensor and configured to transmit an X-ray image obtained by the X-ray image sensor to the mobile radiation imaging apparatus.

24. The mobile radiation imaging apparatus according to claim 1, wherein, when the arrangement of the radiation generation unit is at the storage position is detected by the detecting unit, the control unit is configured to allow the upward motion of the arm in the vertical direction.

25. The mobile radiation imaging apparatus according to claim 1, further comprising a load detection sensor configured to detect an operational force applied by an operator on the arm,
wherein, when the arrangement of the radiation generation unit at the storage position is detected by the detection unit and the operational force is detected, the control unit is configured to release a brake of the supporting member.

26. The mobile radiation imaging apparatus according to claim 1, further comprising a load detection sensor configured to detect an operational force applied by an operator and configured to detect whether an upward force is applied to the supporting member,
wherein, in a case where it is determined that a magnitude of the upward force is larger than a predetermined threshold, the control unit is configured to release a brake of the supporting member.

27. A control method for a mobile radiation generating apparatus, the apparatus including a radiation generation unit, a cart, a supporting member formed on the cart and having an extendable arm which holds the radiation generation unit, and a monitor provided on an upper face side of the cart, the method comprising:
   detecting, with a detecting unit, an arrangement of the radiation generation unit in at a storage position; and
   limiting a motion of a supporting member which arranges the radiation generation unit and sets an irradiated range of radiation according to a result of the detecting,
   wherein, when arrangement of the radiation generation unit at the storage position is detected by the detection unit, the limiting step includes limiting an extension motion of the extendable arm in a horizontal direction while simultaneously allowing an upward motion of the arm in a vertical direction.

28. A mobile radiation imaging apparatus comprising:
   a radiation generation unit configured to generate radiation;
   a cart;
   a supporting member formed on the cart and including an arm which holds the radiation generation unit and is rotatable to tilt the radiation generation unit;
   a detection unit configured to detect arrangement of the radiation generation unit at a storage position;
   a control unit configured to limit a motion of the supporting member according to a detection result by the detection unit; and
   a monitor provided on an upper face side of the cart,
   wherein, when arrangement of the radiation generation unit at the storage position is detected by the detection unit, the control unit limits a rotational motion of the radiation generation unit while simultaneously allowing an upward motion of the arm in a vertical direction.

* * * * *